(12) United States Patent
Sethi

(10) Patent No.: US 9,113,857 B2
(45) Date of Patent: Aug. 25, 2015

(54) SAMPLING CATHETER DEVICES, METHODS, AND SYSTEMS

(71) Applicant: The Trustees of Columbia University in the City of New York, New York, NY (US)

(72) Inventor: Amrita Sethi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/341,978

(22) Filed: Jul. 28, 2014

(65) Prior Publication Data
US 2014/0336528 A1 Nov. 13, 2014

Related U.S. Application Data

(63) Continuation of application No. PCT/US2013/024160, filed on Jan. 31, 2013.

(60) Provisional application No. 61/593,295, filed on Jan. 31, 2012.

(51) Int. Cl.
*A61B 10/00* (2006.01)
*A61B 10/02* (2006.01)
*A61B 10/04* (2006.01)

(52) U.S. Cl.
CPC ......... *A61B 10/0283* (2013.01); *A61B 10/0266* (2013.01); *A61B 10/04* (2013.01); *A61B 2010/0216* (2013.01)

(58) Field of Classification Search
CPC ........... A61B 10/0283; A61B 10/0266; A61B 10/04; A61B 2010/0216

USPC .................................................. 600/562–572
See application file for complete search history.

(56) References Cited

U.S. PATENT DOCUMENTS

| 2,955,591 A | * | 10/1960 | MacLean ................... 600/569 |
| 4,235,244 A | | 11/1980 | Abele et al. |
| 5,056,529 A | * | 10/1991 | de Groot .................... 600/567 |
| 5,601,588 A | * | 2/1997 | Tonomura et al. .......... 606/185 |
| 5,738,109 A | | 4/1998 | Parasher |
| 5,810,744 A | | 9/1998 | Chu et al. |
| 5,895,400 A | | 4/1999 | Abela |

(Continued)

FOREIGN PATENT DOCUMENTS

| WO | WO 97/05826 | 2/1997 |
| WO | WO 01/35839 | 5/2001 |

OTHER PUBLICATIONS

International Search Report and Written Opinion for International Application No. PCT/US13/24160, mailed Apr. 24, 2013.

*Primary Examiner* — Rene Towa
(74) *Attorney, Agent, or Firm* — Miles & Stockbridge P.C.; Mark A. Catan

(57) ABSTRACT

A sampling catheter encloses a sampling brush which can be selectively extended and retracted from and into the catheter assembly to allow insertion and movement of the catheter while presenting a smooth surface to the body lumen. The selective extension and retraction of the brush allows it to be withdrawn while limiting contamination by contact with tissue outside of the sampled region. The catheter may simultaneously or separately house a cutting tool for slice sampling tissue.

16 Claims, 11 Drawing Sheets

(56) References Cited

U.S. PATENT DOCUMENTS

| | | | |
|---|---|---|---|
| 6,641,564 B1 * | 11/2003 | Kraus | 604/164.1 |
| 7,416,555 B2 | 8/2008 | Krivoruchko | |
| 7,871,422 B2 | 1/2011 | Shibata | |
| 2005/0267458 A1 * | 12/2005 | Paul et al. | 606/41 |
| 2008/0243031 A1 | 10/2008 | Seibel et al. | |
| 2010/0168612 A1 | 7/2010 | Ducharme et al. | |
| 2013/0158464 A1 * | 6/2013 | Samoocha et al. | 604/8 |

* cited by examiner

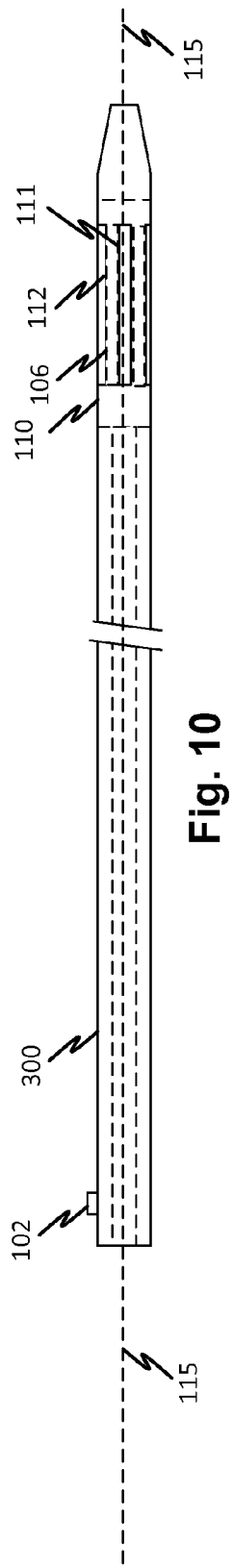
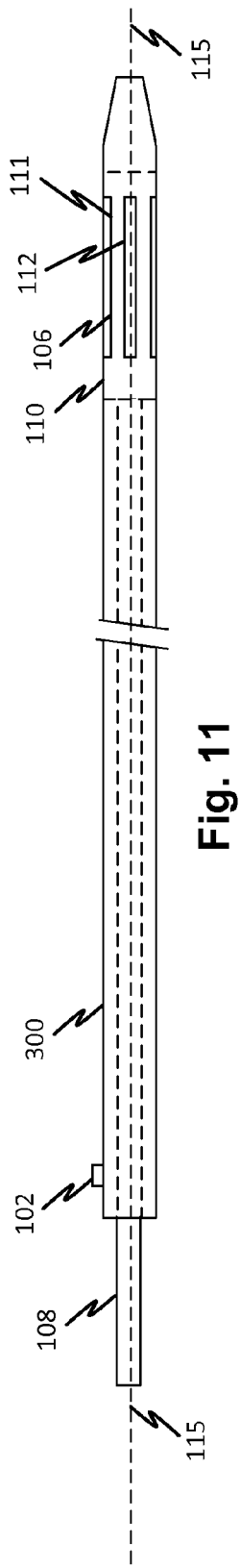
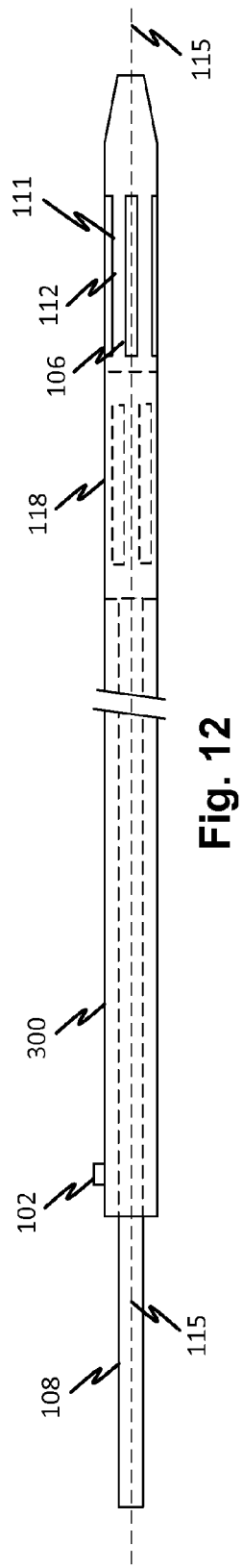
Fig. 10
Fig. 11
Fig. 12

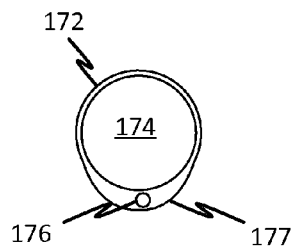
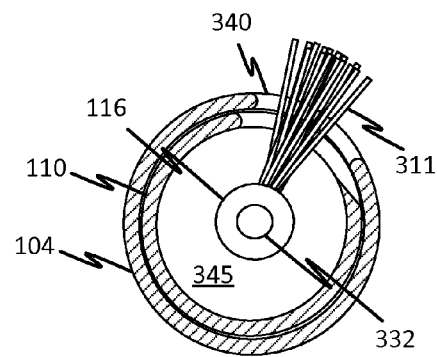
Fig. 13A       Fig. 15
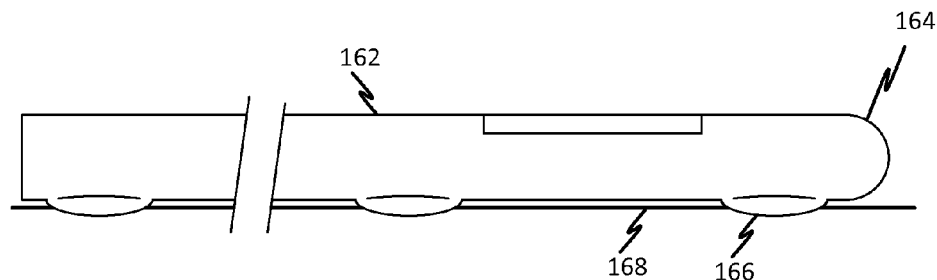
Fig. 13B
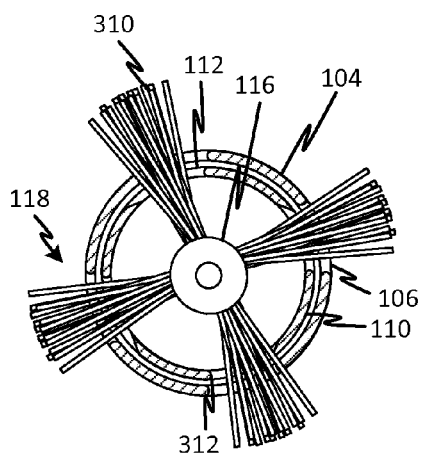 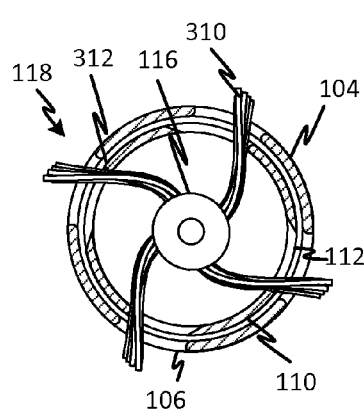 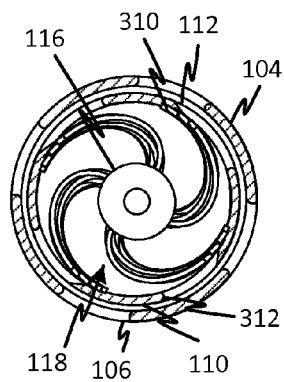
Fig. 14A       Fig. 14B       Fig. 14C

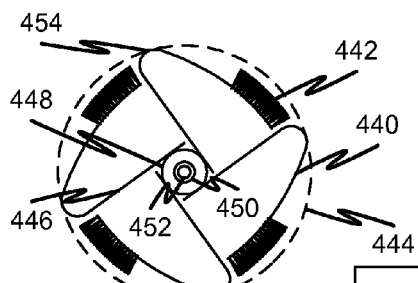
Fig. 17A
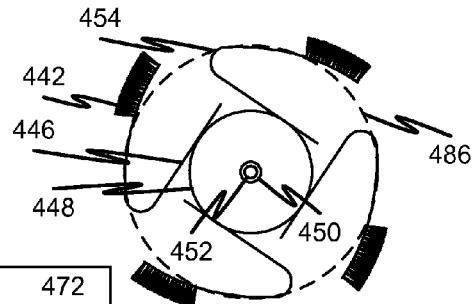
Fig. 17B
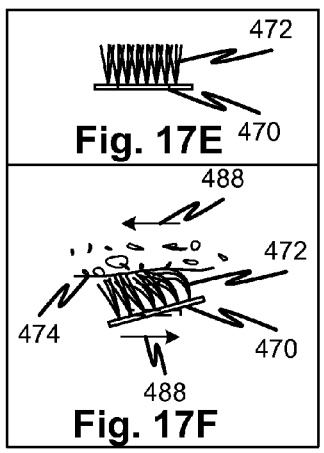
Fig. 17E
Fig. 17F
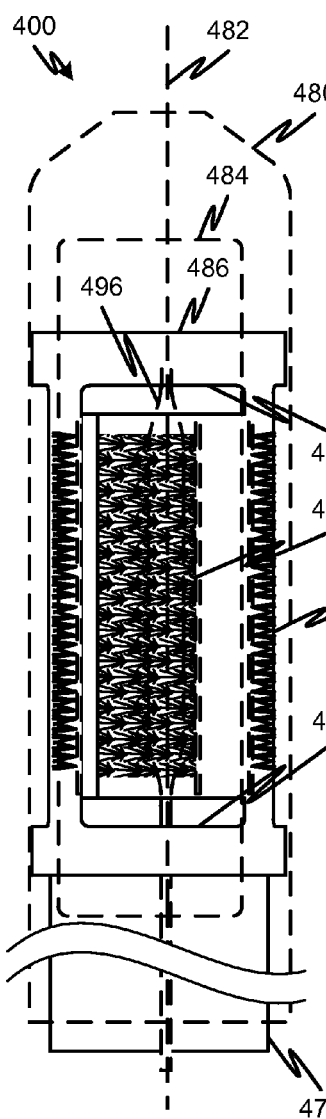
Fig. 17C
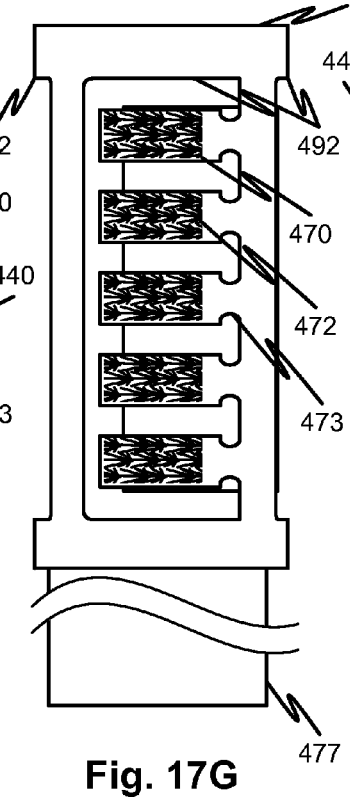
Fig. 17G
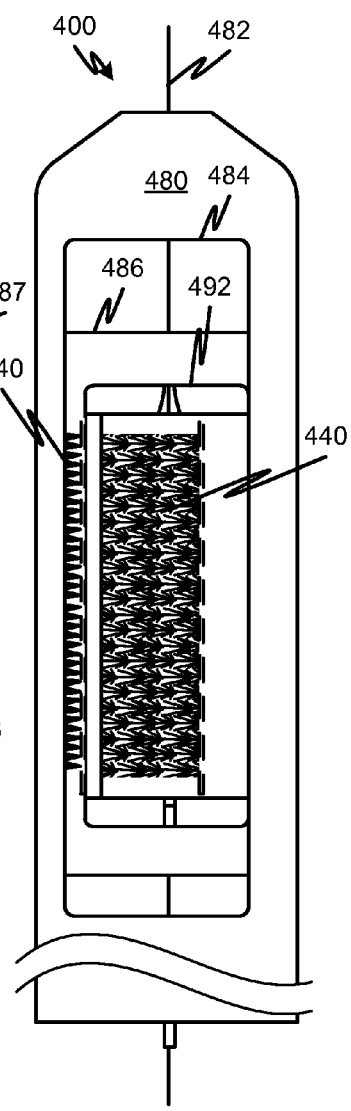
Fig. 17D

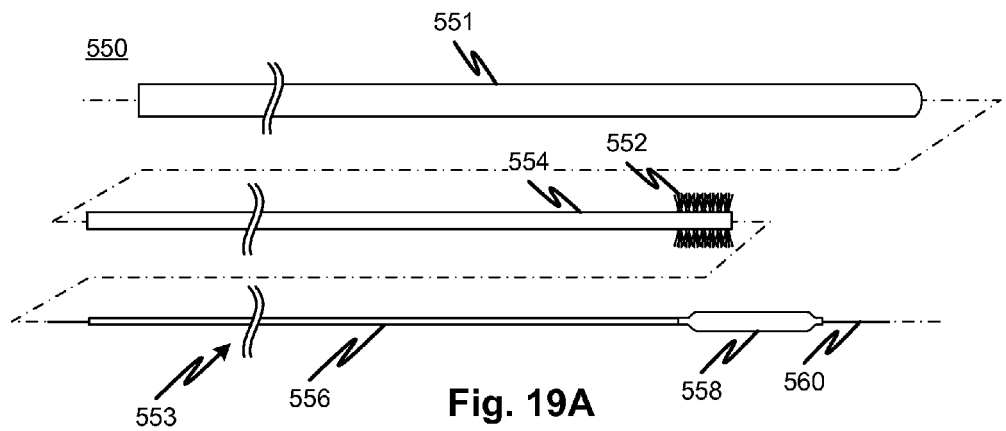
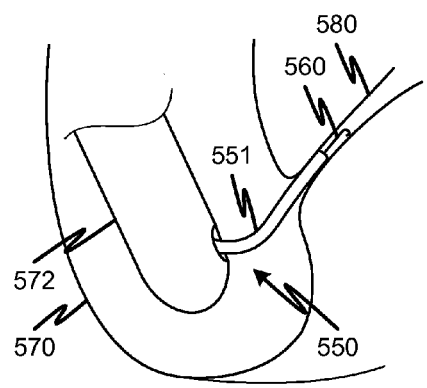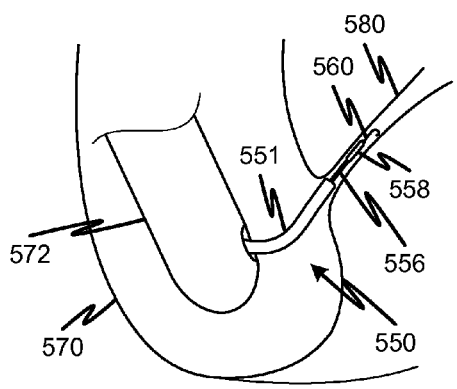
Fig. 19B          Fig. 19C
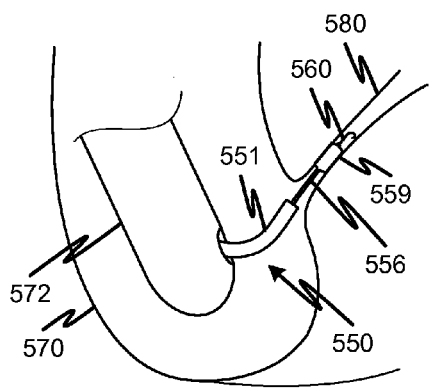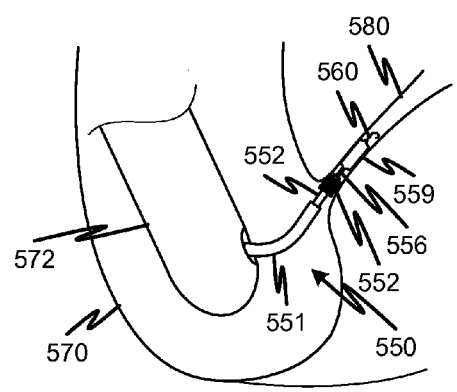
Fig. 19D          Fig. 19E

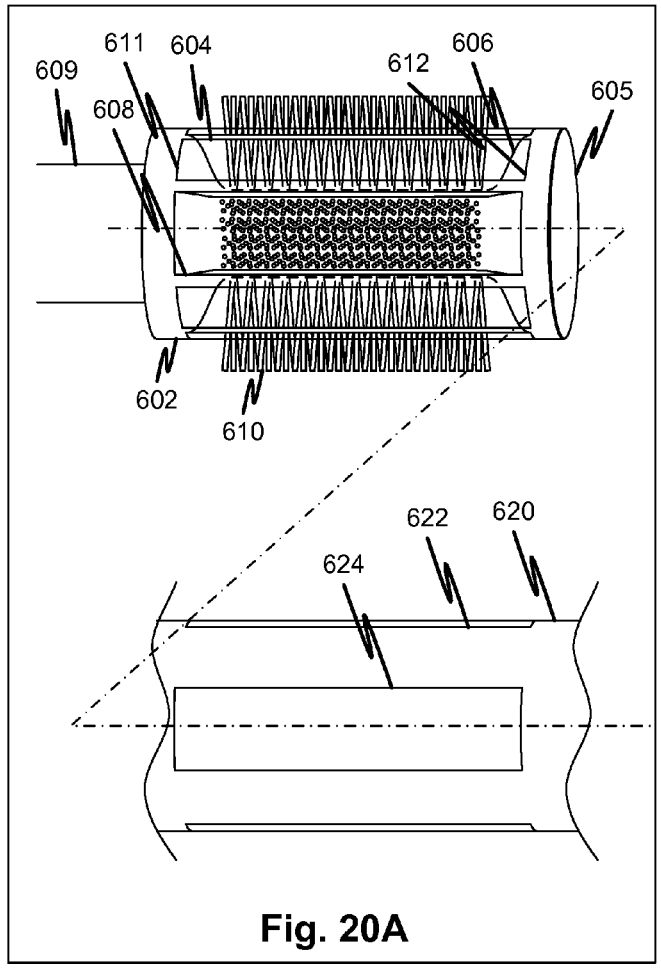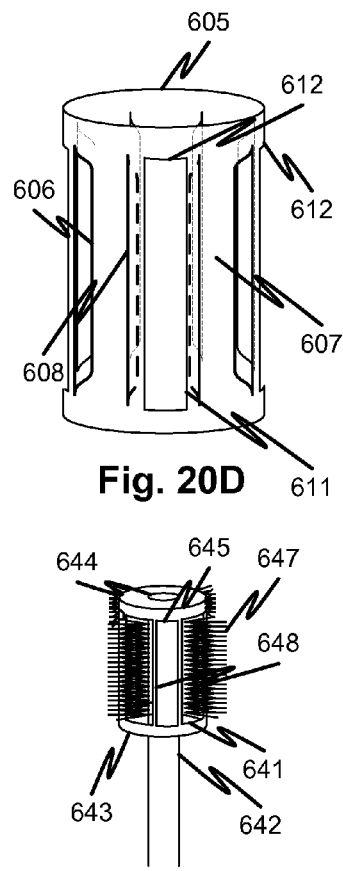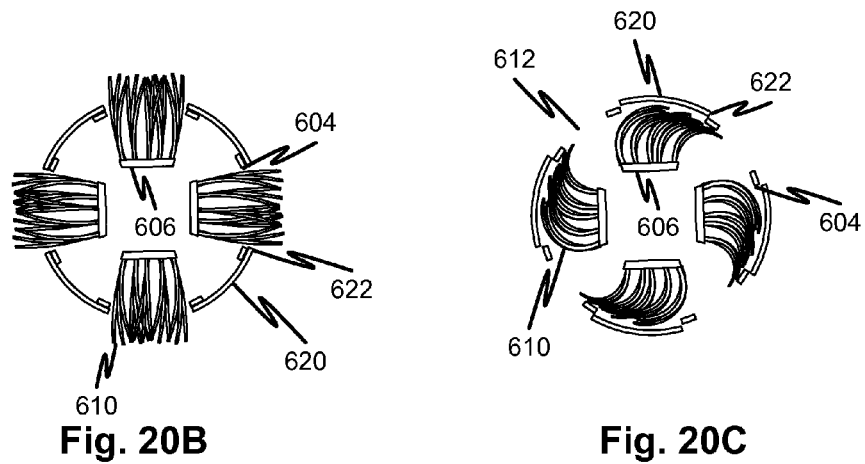
Fig. 20A
Fig. 20D
Fig. 20E
Fig. 20B
Fig. 20C

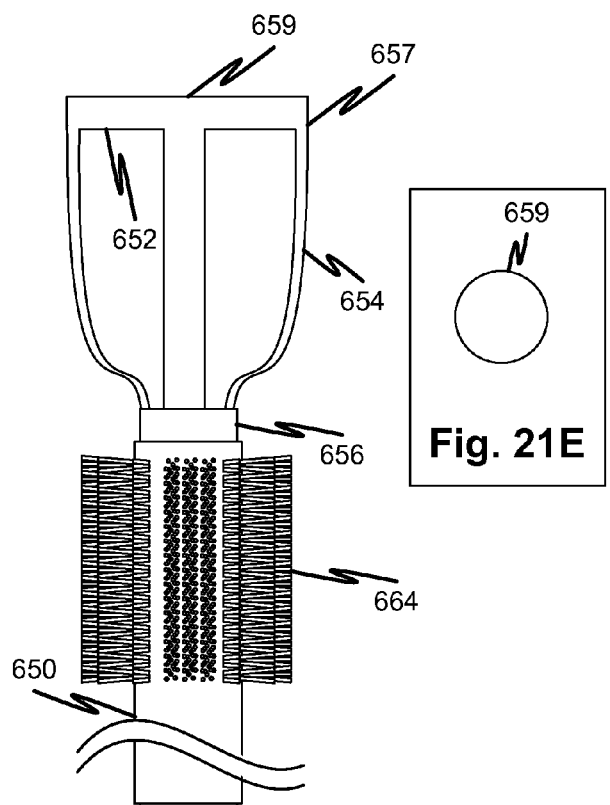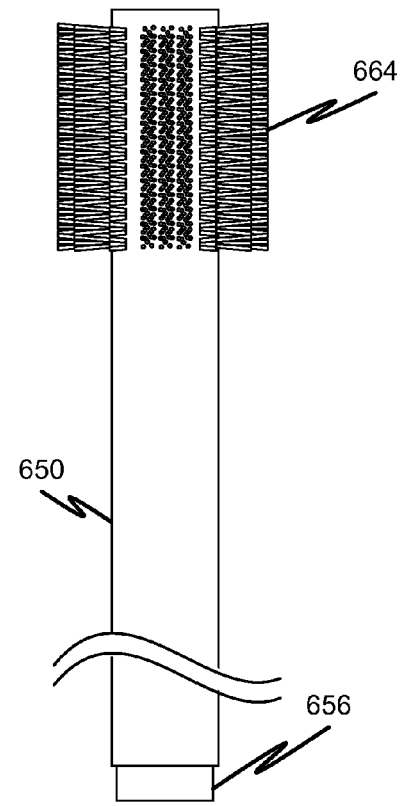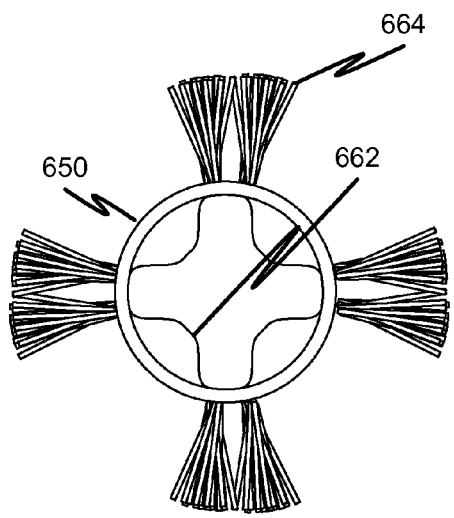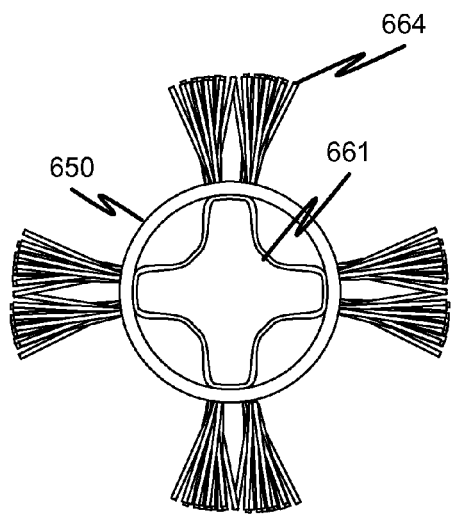
Fig. 21A   Fig. 21B   Fig. 21C   Fig. 21D   Fig. 21E

SAMPLING CATHETER DEVICES, METHODS, AND SYSTEMS

CROSS-REFERENCE TO RELATED APPLICATIONS

The present application is a continuation of International Application No. PCT/US13/24160, filed Jan. 31, 2013, which claims the benefit of U.S. Provisional Application No. 61/593,295, filed Jan. 31, 2012, both of which are hereby incorporated by reference herein in their entireties.

BACKGROUND

Diagnostic sampling catheters are used in the diagnosis of illnesses or for other purposes in which a microbiological sample from a site within a living animal is desired. The microbiological sample, in some catheters, may use a brush to scrape a sampling site to remove a sample of the material or microorganisms at the sampling site. Slicing-type biopsy devices are also known.

SUMMARY

A sampling catheter encloses a sampling brush which can be selectively extended and retracted from and into the catheter assembly to allow insertion and movement of the catheter while presenting a smooth surface to the body lumen. The selective extension and retraction of the brush allows it to be withdrawn while limiting contamination by contact with tissue outside of the sampled region. The catheter may simultaneously or separately house a cutting tool for slice sampling tissue.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 10 shows the elements illustrated in FIGS. 1 and 2 assembled, with the openings of the cutting tool being out of alignment with the ports of the outer sheath, according to embodiments of the disclosed subject matter.

FIG. 11 shows the elements illustrated in FIGS. 1 and 2 assembled, with the openings of the cutting tool being in alignment with the ports of the outer sheath, according to embodiments of the disclosed subject matter.

FIG. 12 shows the elements illustrated in FIGS. 1 and 2 assembled with the cutting tool retracted according to embodiments of the disclosed subject matter.

FIGS. 13A and 13B show features of embodiments which allow a guide wire to be fed through a separate opening from a main lumen of an outer sheath, according to embodiments of the disclosed subject matter.

FIG. 14A shows a section of a catheter with bristles of a brush extended, according to embodiments of the disclosed subject matter.

FIG. 14B shows a section of a catheter with the bristles of a brush partially retracted by rotation of the brush, according to embodiments of the disclosed subject matter.

FIG. 14C shows a section of a catheter with the bristles of a brush fully retracted and a cutting tool rotated relative to the outer sheath, according to embodiments of the disclosed subject matter.

FIG. 15 shows, in section, a brush with a single tuft of bristles and a single opening in a catheter as an alternative to the multiple tuft and opening embodiments, according to embodiments of the disclosed subject matter, the single opening configuration being a variant of all the embodiments disclosed herein except for those lacking a brush.

FIGS. 17A through 17H are for describing embodiments in which a cutting tool carries brush bristles and transitions between brushing and cutting configurations, according to embodiments of the disclosed subject matter.

FIGS. 19A through 19E show, along with related features, a brush catheter arrangement for brushing entrance or branching regions of a lumen, according to embodiments of the disclosed subject matter.

FIGS. 20A through 20E show, along with related features, a combined cutter and brushing tool, according to embodiments of the disclosed subject matter.

FIGS. 21A through 21E show, along with related features, a cutting tool and a brush that slides over it which compresses the cutting tool, according to embodiments of the disclosed subject matter.

DETAILED DESCRIPTION

Referring to the figures, the embodiments include a wire-guided, endoscopic, tapered catheter that contains a brush for obtaining cytology samples, as well as a moveable sheath system that provides at least one or more of the following functions:
1. Penetration of body lumens and selective positioning of a distal end with guidance through curved passages;
2. Shaving and/or entrapment of tissue samples under vacuum with closure by the sheath of a large exposure opening in the catheter;
3. Aspiration of samples through distal ports under vacuum;
4. Brush sampling of cells and/or tissue;
5. Scraping or disruption of tissue using brush bristles or cutting elements;
6. Selective projection and withdrawal of brush bristles;
7. Selective projection and withdrawal of brush bristles through the same openings as used for aspiration and/or cutting of tissue samples;
8. Capture of samples and retrieval thereof; and
9. Isolation of samples to prevention of cross-contamination of, or by, parts of the body.

Figure 1:
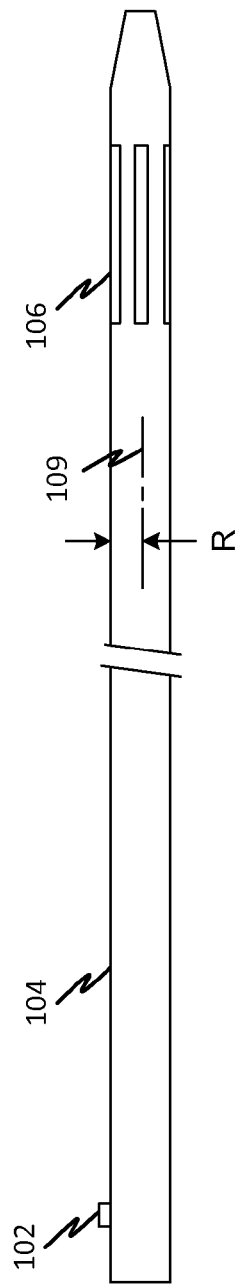
FIG. 1 shows a catheter, which is a hollow cannula or sheath with ports at the end which, in embodiments, serve triple duty as cutting devices, openings for bristles, and the aspiration ports, according to embodiments of the disclosed subject matter.
Figure 2:
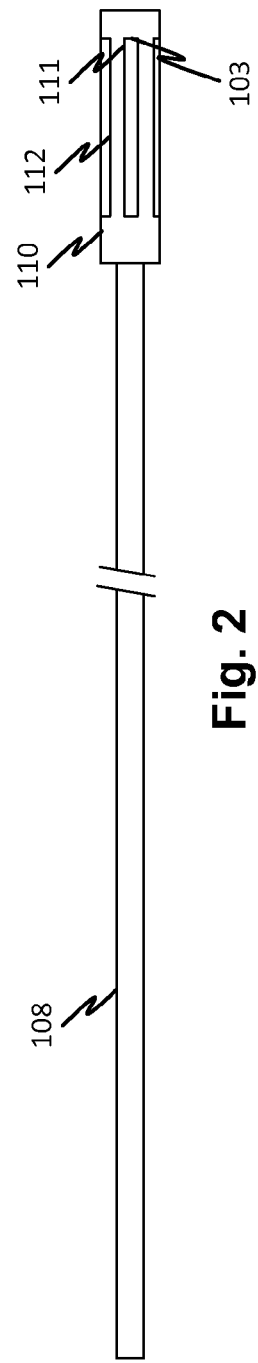
FIG. 2 shows an inner sheath that fits in the hollow cannula of FIG. 1 and has a cutting tool at its end, according to embodiments of the disclosed subject matter.
Figure 3:
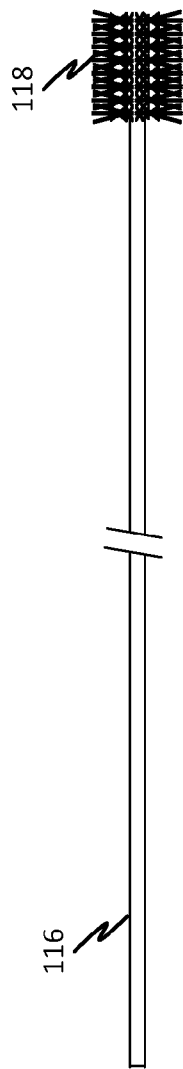
FIG. 3 shows a shaft with a brush it its end whose bristles may be selectively extended through the ports at the end of the cannula of FIG. 1, according to embodiments of the disclosed subject matter.

Referring to FIGS. 1, 2, and 3, a catheter outer sheath or cannula 104 houses an inner sheath 108, which houses a shaft 116. The outer sheath 104 has one or more distal ports 106. The distal ports may have cutting edges to facilitate cutting as discussed below. The distal ports 106 are in flow communication with a proximal aspiration port 102 to which a vacuum may be selectively applied to draw tissue into the distal ports 106. The inner sheath 108 has a cutting tool 110 with one or more openings 111 at least one of which may carry one or more cutting edges 103, 112. The shaft 116 carries, at a distal end thereof, a brush whose bristles may be extended through distal ports 106 and, if inserted simultaneously, the openings 111. The bristles may also be withdrawn from the openings selectively by suitable positioning of the shaft 116 relative to the outer 104 sheath and if present the inner sheath 108.

The outer and inner sheaths 104 and 108 as well as the shaft 116 may be of monolithic or composite construction which may include plastic and/or metal or other suitable materials or combinations thereof according to known materials and structure in the field of medical catheter design. In addition, the outer sheath may have followers for a wire guide (115 in FIGS. 4-12) or may be of an articulating type. The shaft 116 may be hollow or solid. The brush 118 may be of nylon bristles or other material, including metal. The bristles may be fastened to the shaft 116 by means of clips, by an adhesive or potting compound, or by forming a molded part that includes the bristles which fits over the end of the shaft 116.

The catheter may include a variety of functional components to allow it to be articulated and or steered as required. The proximal end may be fitted with controls to permit a surgeon to steer the catheter. These components are known in the art and include, for example, articulation control and one or more wires extending along the catheter. Examples of prior art devices with suitable mechanisms include biopsy sampling devices, endoscopes, laparoscopic instruments, etc. In wire guide embodiments push or pull forces on one or more wires extending along the catheter can curve the catheter to steer the distal end by deflecting it at angles selected by the displacement of the wires. Forces may be applied in other ways, for example by shape memory materials and selective heating, linear motors, artificial muscles that are activated by embedded electrical final control signals, hydraulic bladders, and other devices and methods.

Figure 4:
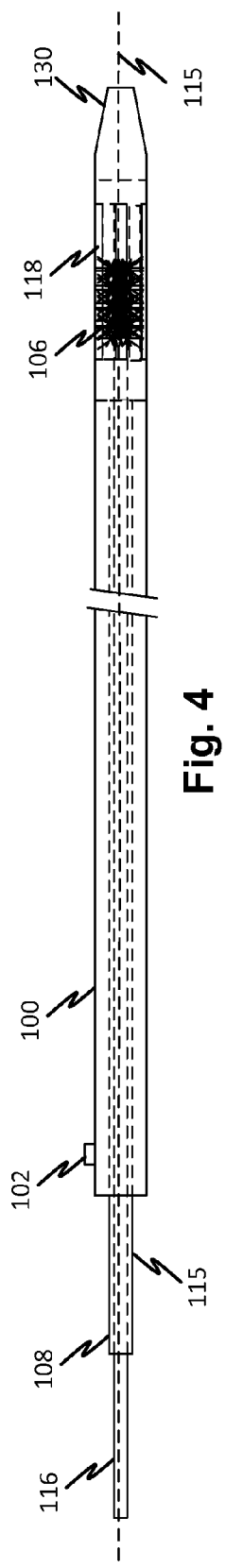
FIG. 4 shows the elements illustrated in FIGS. 1-3 assembled with the brush bristles in an extended but withdrawn configuration, according to embodiments of the disclosed subject matter.
Figure 5:
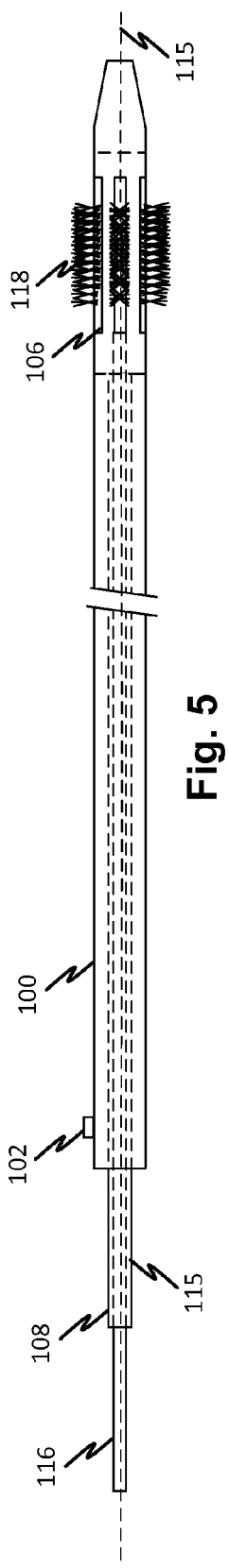
FIG. 5 shows the assembly of FIG. 4 with the brush bristles fully extended, according to embodiments of the disclosed subject matter.
Figure 6:
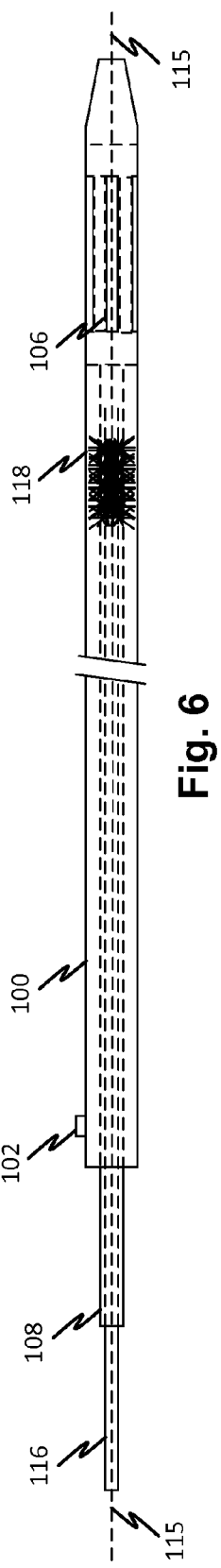
FIG. 6 shows the assembly of FIGS. 4 and 5 with the brush in a retracted configuration to permit cutting of tissue samples, according to embodiments of the disclosed subject matter.
Figure 7:
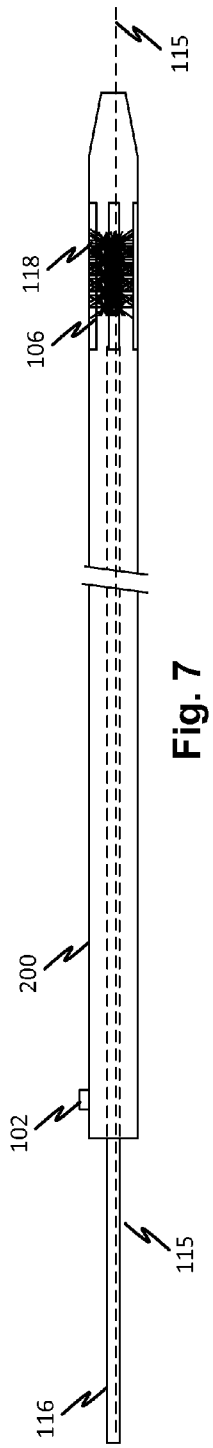
FIG. 7 shows the elements illustrated in FIGS. 1 and 3 assembled with the brush bristles in an extended but withdrawn configuration, according to embodiments of the disclosed subject matter.
Figure 8:
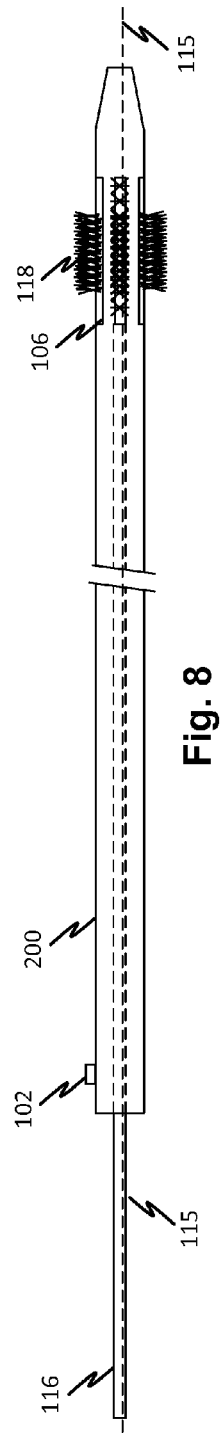
FIG. 8 shows the assembly of FIG. 7 with the brush bristles fully extended, according to embodiments of the disclosed subject matter.
Figure 9:
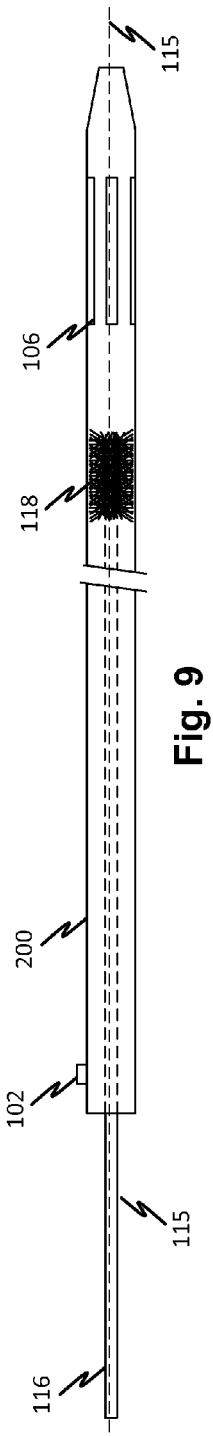
FIG. 9 shows the assembly of FIGS. 7 and 8 with the brush retracted, according to embodiments of the disclosed subject matter.

FIGS. 4, 5, and 6 show a cannula assembled from the elements of FIGS. 1, 2, and 3, namely, the catheter outer sheath 104 houses the inner sheath 108 which houses the shaft 116. FIGS. 7, 8, and 9 show another embodiment in which the shaft 116 is housed only by the outer sheath 104. FIGS. 10, 11, and 12 show another embodiment in which only the inner sheath 116 is housed by the out sheath 104 and used for cutting with aspiration and suction. In addition to illustrating alternative embodiments, FIGS. 7, 8, and 9 and FIGS. 10, 11, and 12 illustrate the functions of the catheter outer sheath 104 with ports 106, the inner sheath 108 with openings 111 and cutting edges 103, 112 and the shaft 116 with a brush 118. In embodiments, the cutting edge 112 may be in the position indicated at 103 to allow tissue to be sliced by moving the cutting tool 110 in the axial direction (toward and away from the distal end along the longitudinal axis of the outer sheath 104). In this way the cutting can be performed by torqueing the inner sheath, drawing, and/or pushing it. Note that cutting edges 103 or 112 can be positioned on the opposite sides of the openings 111 or on both sides. Also the number of openings 111 and the number of cutting edges in each may be varied.

Referring now to FIG. 4, a vacuum may be applied to the proximal aspiration port 102 to generate a vacuum at the distal ports 106 located at the distal end of the outer sheath 104. The catheter 100, which contains the brush 118, can be inserted into a body lumen or stricture which is facilitated by a tapered contour of distal end 130 of the outer sheath 104. Rather than advancing the brush 118 out of the catheter, as in prior art devices, the inner sheath 108 (shown in FIG. 2) is withdrawn (as illustrated in FIGS. 7, 8, and 9), retracted partially (to the position shown in FIG. 12) or rotated as shown in FIG. 5 to align openings 111 with distal ports 106 in order to allow the brush bristles to emerge from within the catheter 100.

In FIG. 5, openings 111 in the inner sheath 108 are aligned with aspiration ports 106 in the outer sheath 104 to expose the bristles of brush 118. In this configuration, brushing may be performed with a forward and backward motion of the catheter 100. In alternative embodiments, the openings 111 and the ports 106 may be configured to permit the brush 118 to be moved back and forth or rotated reciprocally to generate a controlled disruption of the surface of the body lumen into which the catheter 100 is inserted. The catheter 100 may also be rotated as a whole to disrupt the lumen surface. The catheter 100 may be stabilized in position by controlling the proximal portion of the catheter 100.

In FIG. 6, the inner sheath 108 may be translated axially or rotated across the distal ports 106 which results in "shaving" off of tissue from the duct into the catheter. In addition, suction may be applied via the proximal aspiration port 102 to generate a suction at the distal ports 106 to draw tissue into the catheter 104 as the sheath is advanced or rotated across the distal ports 106. This may be done after the brush has been used to disrupt the tissue to be sampled or at any other desired time. Suction may also be applied while disrupting the surface with the brush 118 to suck liquid and scraped cells from the lumen surface.

Referring momentarily also to FIG. 1, in the present and further embodiments an outer sheath (also may be referred to as a housing of the catheter), as outer sheath 104, encloses elements that permit a brush to be presented outside an outer radius R from an axis of the sheath, such as axis 109. It will be evident that this description applies to further embodiment described hereinbelow as well as the present embodiment of a catheter assembly 100 (e.g., as shown in FIG. 4). The outer radius R may be uniform along the length of the catheter housing or may vary along the length. The distal end of the catheter housing (e.g., outer sheath 104) may have a constant radius R and may taper for a final interval of the length of the catheter housing. The bristles may be presented from the distal end of the catheter such that at least some of the bristle tips are positioned at a radial distance from the axis that is greater than the outer radius of the catheter (i.e., the outer radius of the outer sheath or catheter housing). Some bristles may remain inside the outer sheath, for example, bent, and some may be shorter than others.

In method embodiments, the catheter 100 (FIGS. 4, 5, 6), 200 (FIGS. 7, 8, 9), or 300 (FIGS. 10, 11, 12) can be used to obtain tissue from pancreaticobiliary strictures as well as intralumenal lesions within the GI tract via an endoscope. Brush cytology samples are used in Endoscopic Retrograde Cholangiopancreatoscopy (ERCP) to help diagnosis strictures as a first line method of obtaining tissue. The catheter is inserted into the working channel of a duodenoscope during ERCP over a wire, into the bile duct. It is advanced until it traverses the area of interest such as a stricture. Radiopaque markers may indicate the location of the catheter. No additional procedures or technology are required to use this device which makes it available to all endoscopists and those performing ERCP.

The embodiments include one or more of the following features: 1) brush remains within catheter and wire guided, 2) catheter serves as dilator, 3) mechanism for tissue to be "shaved" into catheter, functioning as a biopsy device, 4) potentially rotatable brush, 5) opening for introduction of additional devices such as biopsy forceps. The embodiments may be easier to insert due to improved stiffness and continual wire and catheter guidance, allow for improved accuracy of targeting the area of interest, result in increased amount of tissue to be acquired, provide dilation if needed for correct positioning in the stricture, allows for stability of the brush within the stricture such as in distal bile duct strictures, and allow for introduction of additional sampling tools such as small-caliber biopsy forceps.

Other applications for this invention include wire-guided procedures such as interventional radiologists, pulmonologists, and urologists. To facilitate wire-guided procedures, catheters 100, 200, and/or 300 may be provided with a channel for a guide wire 115.

As discussed, the catheter 100 may be used for increased tissue yield in the sampling of pancreaticobiliary strictures. Housed within the catheter 100 are devices that provide for both brush cytology as well as shaving biopsy tissue. In method embodiments, both types of samples can be obtained in a single insertion maneuver. The configuration allows for dilation of the stricture and maintenance of stability during tissue acquisition. With increased tissue in the sample, the diagnostic accuracy of cytology specimens can be improved.

In the embodiments, various catheters are described herein. The catheter of any embodiment may be no more than 20 mm in diameter. In further embodiments, the catheter of any embodiment may be no more than 15 mm in diameter. In still further embodiments the catheter of any embodiment may be no more than 10 mm in diameter. In still further embodiments, the catheter may be no more than 7 mm in diameter. In still further embodiments, the catheter of any embodiment may be no more than 5 mm in diameter.

In any of these embodiments, the catheter may be configured to be positioned and actuated by an endoscope or other larger instrument that is insertable in the body of an animal. Any embodiments may be implemented as a biliary sampling catheter device. The term sampling may apply to material that is retrieved by the brush bristles or by the slicing feature of the embodiments. The size, proportion, flexibility, and other dimensional aspects may be selected to facilitate insertion in a bile duct (possibly including branching portions thereof). The biliary sampling catheter embodiments may be extended from an endoscope or other support instrument, for example inserted in the intestine of a person. The bristles of some of the embodiments extend from the end of the catheter in a radial direction but remain within the longitudinal extent of the catheter, which distinguishes from embodiments or devices which extend a brush past the distal terminal end of the catheter, as in prior art catheter devices.

The tissue diagnosis of pancreaticobiliary strictures is of critical importance in allowing for appropriate therapy such as chemotherapy or surgery. Current sampling methods during ERCP include brush cytology, forceps biopsy, and fine needle aspiration. Sensitivities of brush cytology specimens are 20-57%. Combining brush specimens and forceps biopsy specimens can increase sensitivity to 55%, however, this requires multiple devices. Directly visualized biopsies, which is another method of sampling, requires use of an additional system that can be costly and requires advanced training, thereby limiting its use.

Another benefit of the embodiments 100 and 200 is the support of the shaft 116 by the outer sheath 104. In some brush cytology devices, the brush is pushed through the end of an endoscope or other catheter device supported on its shaft. The support and controllability of the brush is poor in such systems due to the difficulty of advancing the catheter through the working channel of the endoscope (or catheter) and bile duct. Resistance can be encountered advancing the brush out of the catheter into the stricture. At this point it is no longer wire guided and has tolerance for a limited pushing force. The lack of guidance can also result in the brush veering into another direction and missing the target tissue.

A further function produced by the present apparatus is that the catheter may be positioned once and either brush or cutting devices may be selected and deployed at precisely the same location without having to reacquire the position. This avoids instability or failure to reproduce a position when brushing strictures at a target position as the catheter remains outside the duct. In current brush systems, the brush is the only way to obtain tissue. Systems that allow for multi-modality sampling require insertion of separate devices into the catheter, adding to time and cost. This also results in additional specimens for processing, increasing cost.

The disclosed device and method may improve accuracy of positioning of the brush, allow for multi-modality sampling (brushing and biopsy) with one device during the same maneuver, and increase tissue yield.

According to embodiments, the disclosed subject matter includes a wire-guided catheter with a large hole or opening (i.e., within a circumferential surface of the catheter), which allows for contact by a brush held within the catheter. In a variation of the embodiments, the brush sheath itself may also be wire guided and may lie within the catheter. This catheter may be made of stiffer plastic material than currently available brushes, which may assist in advancing the brush through the endoscope. The tip of the catheter may be tapered which allows for some dilation of tight strictures in order for brushing to occur. Fluoroscopic markers may be visible on the catheter to indicate the exact location of the distal port(s) 106.

The inner sheath 108 may be of tubular construction or may be a panel that can be advanced or rotated across the catheter port or ports. The cutting tool 110 at the end of the inner sheath may be used for shaving tissue that projects into the distal ports 106 as a result of the application of a vacuum or passively due to insertion into a narrow lumen portion. The amount of tissue projecting into the "opening" can be increased by applying suction at an aspiration port at the distal end of the catheter. The sheath may be a part of the catheter forming a unitary device.

The brush 118 may remain within the catheter at all times as opposed to being projected outside of the catheter as with other cytology brush devices. The bristles extend out of the distal ports 106 of the outer catheter 104 when the inner sheath 108 is withdrawn or rotated, thus exposing the stricture to the brush. This technique may be used to ensure that the brush is targeting the area of interest at all times. The brush use is facilitated given that the brush alone does not have to be pushed through the tissue, but rather can move freely within the catheter. In embodiments, the shaft may be constructed to permit torque to be transferred along its length from a manipulation end (proximal end) of the catheter to the brush 118. By maintaining the brush within the catheter, there may be greater retention of the tissue acquired.

The guide wire 115 can pass through a central opening of the outer sheath with a distal opening at an end thereof or it can pass through a separate opening of the outer sheath that is isolated from the inner lumen of the outer sheath. In the latter case, the outer sheath can convey a vacuum applied at the proximal port to the distal port(s). Note that self-sealing openings can be provided to allow the proximal ends of shaft 116 to pass through the inner sheath 108 while providing a vacuum seal. Similarly a seal may be provided for the inner sheath 108 to pass through the outer sheath 104 while permitting a vacuum to be sustained within the outer sheath. In alternative embodiments, the vacuum may be applied only to the inner sheath 108 and the cutting tool 110 may form a close fit to the inner lumen of the outer sheath thereby permitting a vacuum to be conveyed to the openings 111 in the cutting tool 110. In this case the brush may remain within the cutting tool 110 and be selectively permitted to extend out of the openings 111 when the openings 111 are rotated so that they coincide with distal ports 106.

In alternative embodiments, the outer sheath 104 may be guided into a target body structure and the inner sheath 108 with the shaft 118 inserted afterward. A guide wire 115 may be inserted and the outer sheath 104 guided by the inserted guide wire 115. Then the guide wire 115 may be withdrawn and the inner sheath 108 with the shaft 118 inserted. In alternative embodiments, the entire catheter 100, 200, or 300 may be guided by the guide wire 115 since spaces may exist to accommodate the guide wire 115. It should clear by inspection that a variety of channels may remain with both the inner sheath 108 and the shaft 118 inserted in the outer sheath 104.

Referring to FIG. 13A, an embodiment of an outer sheath 172 is shown in cross-section. The outer sheath 172 may be used in place of outer sheath 104 in embodiments. Sheath 174 has a lumen 174, a thin outer wall portion 172, and a thicker outer wall portion 177, which is thick enough to permit an additional lumen 176 to be provided for passage of a guide wire 115. The thickened portion 177 may be provided continuously along the length of the catheter to permit it to be manufactured as an extrusion or may be provided at intervals along the length of a sheath 162 as indicated at 166 in FIG. 13B. A closed end 164 may be provided on the catheter. The guide wire is indicated at 168.

At the proximal end of the catheter embodiments 100, 200, or 300 may be any type of control or primary support structure, for example, an endoscope. Various user interface configurations are known for axially displacing or applying torque to elongate structures such as shaft 116 and sheaths 108 and 104.

Referring to FIGS. 14A, 14B, and 14C, note in embodiments, the extension of bristles 310 of the brush 110 past the distal ports 106 in the distal end of the outer sheath 104 can be facilitated by rotating the shaft 116 back and forth to help the bristles "find" a way out of the openings 112 in the cutting tool 110 and the distal ports 106 in the outer sheath 104. Retraction of the bristles 310 can be facilitated by rotating against a non-cutting edge 312 of the openings in the cutting tool 110 as illustrated. FIG. 14A shows the bristles 310 of a brush 118 extended. FIG. 14B shows the bristles 310 of a brush 118 partially retracted by rotation of the brush. FIG. 14C shows the bristles 310 of a brush 118 fully retracted and the cutting tool rotated relative to the outer sheath. Retraction may be achieved in embodiments by moving the brush axially, in addition to or instead of rotating it, to accomplish both extension and retraction of the bristles.

FIG. 15 shows, in section, a brush with a single tuft 311 of bristles and a single opening 340 in a catheter with an outer sheath 104. The cutting tool 110 may or may not be present in alternative embodiments. A feature of the present shaft 116 which supports the tuft 311 of bristles is that it is hollow to provide a lumen 332 for passage of a guide wire 115. This feature may be applied to any of the foregoing embodiments having a brush. Where the shaft 116 has a lumen, a seal may be provided which isolates the lumen 332 from the annular space 345 between the shaft 116 and the outer sheath 104 allowing a vacuum to be applied to the annular space 345 and thereby to suck particles or liquid into the opening 340. The configurations of FIG. 15 are alternatives to the multiple tuft/multiple opening embodiments such as described elsewhere. The single opening configuration being a variant of all the embodiments disclosed herein except for those lacking a brush. The features of FIG. 15 such as the lumen 332 may be applied to other embodiments including those with multiple tufts and multiple openings in the distal end of the catheter.

Figure 16A:
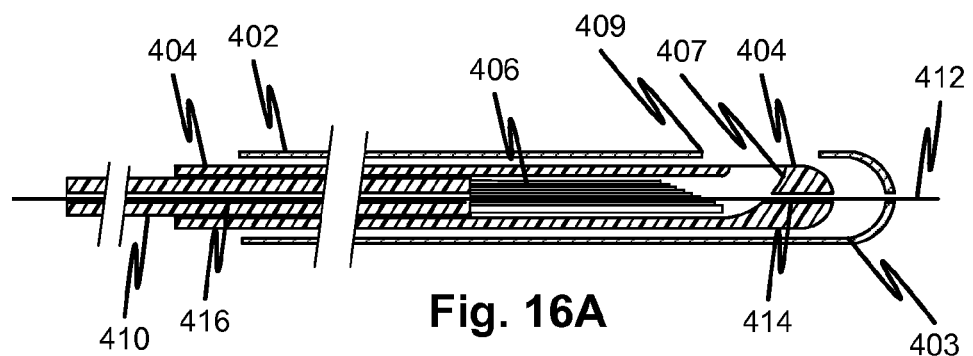
FIGS. 16A to 16C describe embodiments in which brush bristles are aligned with a catheter axis and bent into a radial alignment at their tips when they will be used for brushing, according to embodiments of the disclosed subject matter.
Figure 16B:
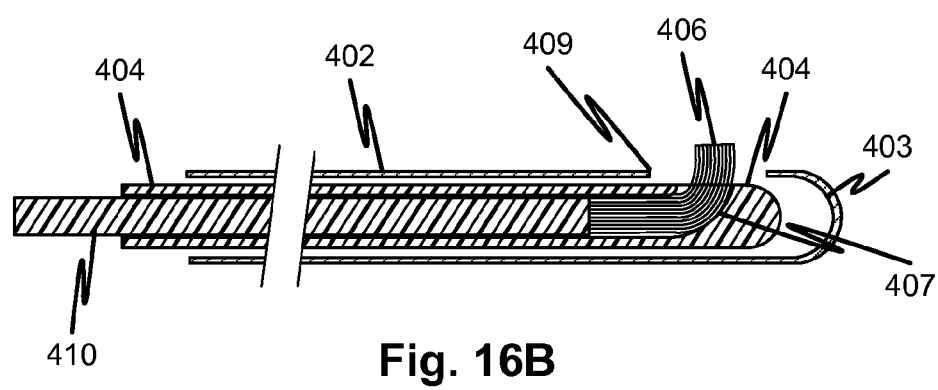
Figure 16C:
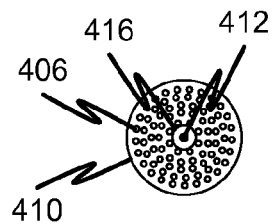

FIGS. 16A to 16C show a brush catheter with an outer sheath 402 and an inner sheath 404. A shaft 410 carries axially aligned bristles 406. The bristles 406 lie in a channel 407 that curves toward the radial direction such that when the shaft 410 is advanced relative to the inner sheath 404, the bristles 406 bend in the radial direction and extend radially through an opening 409 in the outer sheath 402. The sheaths 402, 404, and/or 410 may be wire-guided and a guide wire 412 is shown in FIG. 16A. Alternative embodiments may be non-wire guided and this feature is illustrated in FIG. 16B. FIG. 16B shows the bristles 406 bent and extended radially. In the latter configuration, the inner sheath 404 may be moved axially back and forth to capture material from a body lumen. Thus, room to accommodate this motion may be provided in the shape and or size of the space 403 within the outer sheath 402. FIG. 16C shows an end view of the shaft 410 with the bristles 406 extending toward the viewer. A hole 416 accommodates a guide wire 412. It will be observed that the bristles 406 may be extended as described without being inhibited by a guide wire 412, if present.

FIGS. 17A through 17D show a catheter 400 with an outer sheath 480 that carries a cutting tool 487 with brush bristles 442 that extend from resilient members 440 attached at respective points 454 to the cutting tool 486 which is generally cylindrical in shape. The cutting tool 486 (as well as cutting tool 487 discussed below) is supported on the end of a sheath 477 which allows it to be moved back and forth axially as well as moved in a single cutting direction by forces applied from the proximal end by an operator. The cutting tool 486 has multiple openings 493 each having a cutting edge 492, which is preferably razor sharp. In embodiments, the cutting edge 492 may be an edge of a separate element blade portion of metal that is attached or molded into a cutting tool of polymer material to make the cutting tool more flexible to facilitate navigation in tortuous body lumens. The outer sheath 480 has openings 484 that allow the bristles 442 to make contact with a body lumen into which the catheter 400 is inserted. The resilient members 440 urge the brush bristles 442 outwardly radially when a balloon 448 is expanded from the configuration of FIG. 17A to that of FIG. 17B. FIGS. 17A and 17B show sections at a point in the middle of the cutting tool 486. The assembly may be wire guided, a guide wire being indicated at 482.

Figure 17H:
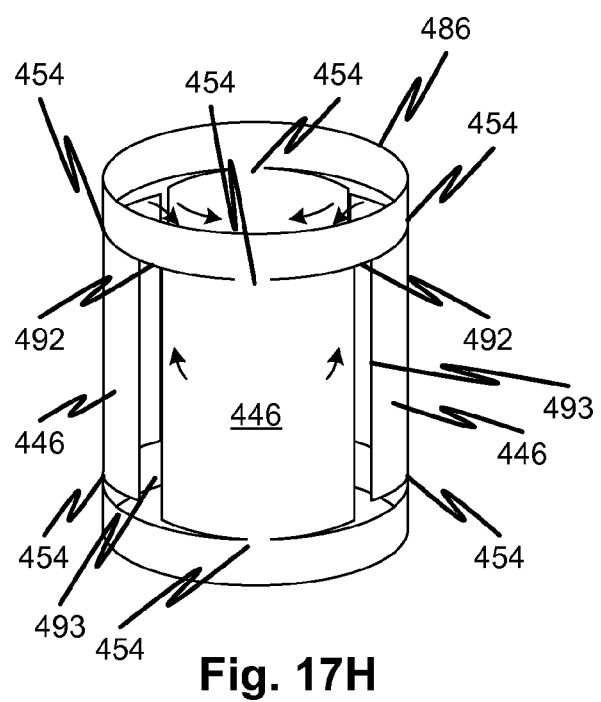

As shown in FIG. 17H, the resilient members 446 may be formed as leaf springs and may be defined, at least in part, by cutting the wall of the cutting tool 486 or attached as separate elements, for example by laser cutting a high strength material such as nickel-titanium allow used in medical stents. As illustrated the resilient members 446 are attached at the ends thereof at respective points indicated in the cross-section view at 454 and in FIG. 17H. These may be laser cut from the walls of the cylinder making up the cutting tool 486 which may be bent inward, for example as illustrated by the arrows in FIG. 17H. In embodiments, the cut out walls may be cut as interlacing fingers extending circumferentially from a line connecting two points 454 that are separated axially to allow them to extend further from the points 454 to provide a large enough radial dimension to reach toward the balloon 448 and lever the brush bristles 442 as illustrated in FIGS. 17A and 17B. In other embodiments, the resilient members 446 may be made from separate elements that are attached by a hinging device on the inside of the body of the cylindrical cutting tool to achieve a similar effect. Still other alternatives are possible such as attaching the brushes directly to the balloon 448 with an intervening spring and providing open openings 492 on the cutting tool to allow the brush bristles to extend beyond the walls of the body of cylindrical cutting tool 486. In this case the balloon may be star-shaped so that portions of it contact and press against solid parts of the cutting tool to brace it against the cutting tool.

The balloon 448 may be any type of expanding element suitable for the disclosed function. In the embodiment, the balloon 448 may be carried on a shaft 450 having a hole 452 for a guide wire. As is known balloon catheter designs, the balloon may be fed from its proximal end by a pumped fluid using known appliances and systems, for example endoscopic instruments as known in the medical field.

In the embodiment of FIG. 17G, the portion of the resilient members 446 that support the brush bristles 442 has been cut into fingers 470 with narrowed necks 473. This configuration permits the fingers 470 to feather as illustrated by FIGS. 17E and 17F when rubbed (by moving the cutting tool in the axial direction—relative motion indicated by arrows 488) against the wall 474 of a body lumen. Here the bristles 472 yield by bending while the fingers 470 yield by pivoting (as shown in FIG. 17F) at the neck, which may be characterized as "feathering." The combination of the bending of the short bristles and the feathering, as well as the radial compliance of the fingers 470 makes the bristles 472 yield more like longer brush bristles.

In the embodiments discussed with reference to FIGS. 17A through 17H, a vacuum may be applied at the proximal end of the outer sheath 480 to draw tissue into the openings 484. The expanding element may be reduced in size, for example, the balloon 448 may be deflated. The bristles 442, 472 are thus retracted from the openings 484. This allows the tissue of the body lumen to extend below the cutting edge to permit slicing. The cutting edge 492 of cutting tool 486 or 487 or any of the alternative embodiments may be moved in the proximal direction from a point distal of the openings 484 so as to slice the tissue from the body lumen. The openings in the outer sheaths of these embodiments facilitates the slicing by the edge of the window serving to support the tissue against the force of cutting.

The embodiments discussed above in which a cutting tool carries bristles (or in which a balloon carries but is braced thereagainst), the single sheath 477 is used to apply forces to both the bristles and the cutting edge used for slicing. As a result, the configurations avoid the need to provide two sheaths or shafts, one to support the brush and the other to support the cutting edge of the cutting tool. This allows an improved balance between stiffness required for manipulating the brush from the proximal end (i.e., reduced axial compliance) and the need for the catheter assembly (e.g., 400) to be flexible in order to navigate tortuous body lumens.

Figure 18A:
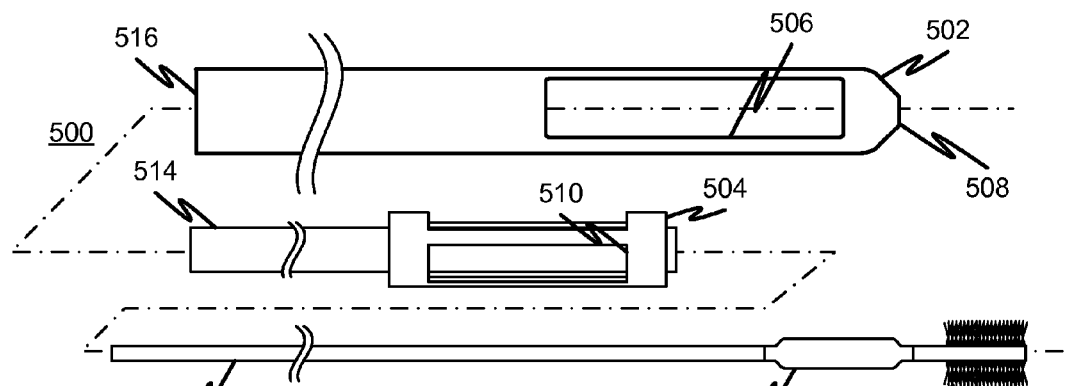
FIGS. 18A through 18D show, along with related features, embodiments in which a balloon is used to change the stiffness properties of portions of a brush catheter, according to embodiments of the disclosed subject matter.
Figure 18B:
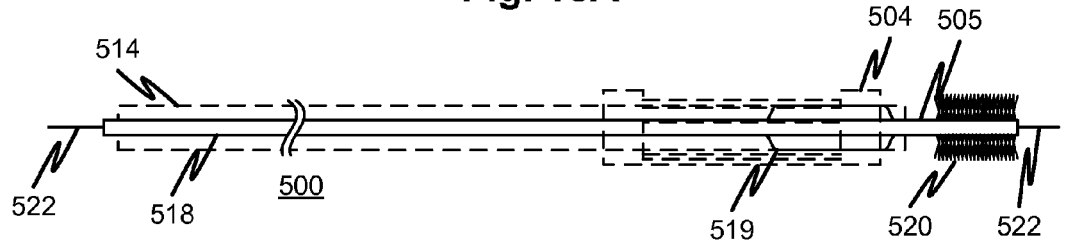
Figure 18C:
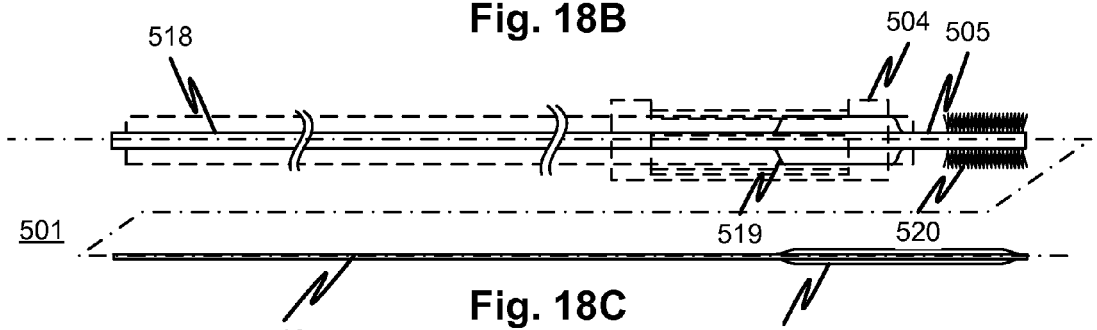
Figure 18D:

Referring to FIG. 18A, an outer sheath 502 has openings 506 for slicing tissue of a body lumen. An inner sheath 514 supports a cutting tool 504 at its distal end. The cutting tool has a cutting edge 510 that may be used to slice tissue drawn into the openings 506 or forced thereinto from the outside. An opening 508 at the outer sheath 502 distal end is configured to allow a brush to extend therethrough. One of the problems with prior art brush catheters that are extended through the distal of a sheath is that they are supported on flexible shafts that have too much compliance along their lengths to allow them to be manipulated from the proximal end of the catheter. In the present embodiment, this problem is mitigated by bracing the shaft 518 that carries the brush 520 using a balloon 519 which inflates to press against the interior of the sheath 514 carrying the cutting tool 504 as shown in FIG. 18B. The catheter 510 may be guided by a guide wire 522 passing through the shaft 518. This arrangement allows the brush 520 to be manipulated from the proximal end via the inner sheath 514 because displacements thereof may be transmitted with little compliance owing to the grip of the balloon 519 on the sheath 514. In a variation, the segment 505 of the shaft 514 may have a higher rigidity than the shaft 514 as a whole thereby reducing compliance between the shaft 514 and the brush 520. FIGS. 18C and 18D show a variation of the present design in which an additional balloon catheter 501 with a balloon 540 supported on a shaft 542 is inserted within the shaft 518 (as shown in FIG. 18D). In this case, the guide wire may pass through the shaft 542. The balloon 540 may form a bridge of rigidity between the distal end of the inner sheath 514 and the brush when required at a time the brush 520 is to be manipulated. Here both balloon 519 and 540 convey the forces applied to the proximal end of the shaft 514 to the brush 520. This may permit the shafts 542 and 518 to be made more flexible thereby contributing to the flexibility of the catheter 500 as a whole, making navigation of tortuous channels easier. As will be seen the balloon 540 may serve the same function as the balloon 558 (See FIG. 19A et seq.) as described next.

FIG. 19A shows catheter 550 with an outer sheath 551 that encloses an inner sheath 554 carrying a brush 552 at its distal end. A balloon catheter 553 has a shaft 556 extending through the inner sheath 554 and movable such that its distal end can project through the end of the inner sheath 554 distal of the brush 552. The relative movement is accomplished by manipulation of the proximal ends of the inner 554 and outer 551 sheaths and the shaft 556 according to known principles for actuating surgical and diagnostic instruments. FIGS. 19B through 19E illustrate stages of use of the catheter 550. An endoscope projects the catheter 550 toward a body lumen 580 after guiding the guide wire 560 thereinto. The directing of a guide wire is not discussed because this practice is well supported in the prior art. As shown in FIG. 19B, the outer sheath 551 may be extended to dilate the lumen and/or to support the positioning of the balloon 558 which is extended along the guide wire 560 into the lumen and positioned. The outer sheath 551 may be used for indicating position, for example if it carries indicators visible under fluoroscopy. As shown in FIG. 19C, the balloon 558 is extended into the lumen 580 from the inner 554 sheath and projects beyond the outer sheath 551 by applying traction force to the shaft 556. The balloon 558 is then inflated as shown in FIG. 19B providing an anchor for shaft 556. Then the inner sheath 552 rides along the shaft 556 to brush the mouth 552 of the body lumen as indicated in FIG. 19E. The configuration addresses the problem of brushing a region of a body where a lumen extends from a chamber or canal or in which a lumen branches. Without supporting the catheter in position the brush could not be assured of remaining at the mouth of the body lumen. It will be seen that the present configuration addresses this concern.

FIGS. 20A through 20C disclose features of an embodiment of a combined cutter and brushing tool. In the embodiment, a cutting tool 605 is encased inside an outer sheath 620 in a manner similar to elsewhere described embodiments except that in this case, brush bristles are directly attached to short-radius portions 606 of the cutting tool 605 at a smaller radial distance from its axis than cutting edges 612 thereof. As explained, but avoiding separate elements, a single shaft 609 may be used thereby providing more overall stiffness for cutting and brushing than if separate shafts or sheaths were used for each. This improves the flexibility of the catheter (combination of the cutting tool, brush, and shafts/sheaths). As in prior embodiments, openings 624 are provided in the outer sheath 620. The cutting tool 605 has openings 608 for the brush bristles which stem from the portions 606. The short-radius portions 606 may be formed from a generally cylindrical member as illustrated in FIG. 20D in which openings 608 have been cut for the short-radius portions 606 and the short-radius portions formed from the cuts by pushing inwardly toward the cylindrical axis thereby creating the smaller radial distance from the axis of the cutting tool 605. Openings 611 may also be cut for forming the cutting edge 612 and providing access for a tissue portion from a body lumen to be sliced. The bristles 610 may be attached by any suitable means, including welding metal bristles, epoxy or other adhesive bonding, potting, etc. Advantages of the smaller radial distance is that the bristles may be longer as illustrated in the cross-section view of FIG. 20B and also enabled to be pushed aside to allow for cutting as illustrated in the cross-section view of FIG. 20C. Since the shaft 609 can be stiffer than in a multiple shaft/sheath embodiment, as explained above, it may be formed to provide torque transmitted from the proximal end. The shaft 609, when rotated relative to the outer sheath 620, bends the brush bristles 610 aside and aligns the openings 611 of the cutting tool 605 with the openings 612 of the outer sheath 620 as illustrated in FIG. 20C. In this configuration, the cutting tool 605 may be used to slice tissue by drawing it in a proximal direction within the outer sheath 620 while maintaining the latter in position relative to the body lumen, as in other embodiments. The slicing may be done under a vacuum or if external pressure is sufficient to push tissue into position to be sliced, in the absence of a vacuum.

FIG. 20E illustrates another way to obtain a combined cutting tool 643 and brush in which the cutting edge 645 is at one radial distance from the axis while the brush bristles 647 are supported from the surface of the shaft 642 or another radial distance that is smaller than that of the cutting edge 645 so that they extend outwardly to function in a manner that is as described relative to the embodiment of FIGS. 20A to 20C. The cutting tool 643 may be attached to the shaft 642 directly. An opening 644 may be provided for a guide wire. Openings 648 may be provided to allow tissue to be accessed by the cutting edges 645 as well as openings 641 through which the bristles 647 extend. The embodiment of FIG. 20E may be employed in the same manner as that of FIGS. 20A to 20C and provides similar advantages.

FIGS. 21A through 21D show a cutting tool 657, supported on a shaft 656, that is selectively squeezed within a brush 664 bearing sheath 650 by sliding the latter over the cutting tool 657 from the position shown in FIG. 21A to that shown in FIG. 21B. The bristles 664 may be attached to the sheath 650 in any suitable manner. As shown in the cross-section view of FIG. 21C, the sheath 650 may have internal features 662 to facilitate the squeezing of the cutting tool 657 thereinto, for example sloping ridges that progressively cause a ring shaped portion 659 at the top of the cutting tool 657 (shown in cross section in FIG. 21E) into a folded shape 661 seen in the cross-section view of FIG. 21D. Note that FIG. 21D shows the cross-section of the arrangement of FIG. 21B in the region of the brush bristles 664.

In most of the embodiments, the number of cutting tool openings whose one or more edges has a cutting edge, is the same in number as a number of brush portions, however the numbers need not be the same. For example, in the embodiment of FIG. 20A, the openings 611 and 608 may differ in number. Also the number of openings in the outer sheaths of the embodiments may be different in number from the openings in the cutting tools to form varied embodiments. Also the openings of the sheaths and cutting tool need not be symmetrically positioned or equally spaced therearound. They may also be diagonal, or offset in various ways to achieve similar functions as described herein.

In any of the above embodiments, the outer sheath, for example sheath 104, may be provided with fluoroscopy-revealed markers (fiducials) to facilitate positioning of the distal port. In any of the above embodiments, any inner sheath or shaft may be provided with fluoroscopy-revealed markers (fiducials) to facilitate positioning of a brush, a cutting tool (which may be combined with a brush in embodiments as described above), or a balloon effecter. In any of the embodiments, instead of using a vacuum to draw tissue into a sheath to slice it, if the outer sheath is large relative to a resting size of the body lumen into which it is extended, the pressure from the body may be sufficient to cause the tissue to extend into the outer sheath openings to be sliced.

The longitudinal members generally referred to herein as sheaths and shafts of the respective embodiments may be of any suitable configuration including metal, plastic, or combinations thereof. Their major lengths may be of one material while distal and/or proximal ends may be of a different material or composition of multiple materials in order to provide different properties such as flexibility, torque or compression or tensile compliance, etc. The terms shaft and sheath, in the present context, are not mutually exclusive terms as used herein. In the embodiments, either may have a lumen therethrough. The term shaft has been used where, in variations of the embodiment, a lumen may not be present, for example, an innermost longitudinal member in an assembly.

In any of the disclosed embodiments, tissue may bulge into at least one opening in a distal end of the catheter forming a protrusion to be sliced as described according to the various embodiments. In any of the disclosed embodiments, a majority of the bristles at the distal end of the catheter may be positioned proximal of the very distal end of the catheter such that the bristles receive mechanical support from the catheter itself, including the catheter outer sheath, according to embodiments.

In the embodiments, a brush and cutting tool may reside simultaneously in the catheter or may be removed and inserted at separate times, according to respective apparatus embodiments and/or methods of use. In embodiments, the cutting tool carries bristles and is selectively reconfigurable between a cutting configuration and a brushing configuration. In the cutting configuration, the bristles are radially retracted. In the brushing configuration, the bristles are radially extended.

It will be evident that in many of the embodiments, the cutting tool and brush are movable within the sheath such that they can switch places, whereby the cutting tool can be used for cutting tissue extending through one or more openings in the outer sheath (or the catheter) and the brush can be used for brushing a body lumen into which the catheter is inserted without fully removing either the brush or the cutting tool from the catheter.

In alternative embodiments, the brush bristles may be replaced by other types of collection devices, depending on the embodiment. For example, an expandable screen may be used for collection by a brushing motion and may be extended from the distal end of the outer sheath.

Note that in any of the embodiments, the outer sheath distal openings may be made longer than the brushes to permit the brushes to be moved axially back and forth in order to gather sample material. Alternatively, the brush or brushes may remain fixed with respect to the outer sheath and the entire outer sheath moved to brush the surface of the body lumen.

According to first embodiments, the disclosed subject matter includes a sampling device with an elongate outer sheath that simultaneously houses a brush and a cutting tool. The sheath is generally adapted for sterilization and insertion in a living person in a manner of surgical instruments. The assembly may form an catheter and delivered as a disposable in a sterile package. In this embodiment, the elongate outer sheath, the brush, and the cutting tool having distal and proximal ends with the brush and cutting tool each having a portion extending over substantially an entire length of the outer sheath. The brush and cutting tool are configured such that each can be manipulated at a respective proximal end thereof to permit the cutting tool to cut tissue samples at the distal outer sheath end and to permit the brush selectively to extend outside the outer sheath distal end and retreat back into the outer sheath.

Any of the first embodiments may be modified, where possible, to form additional first embodiments in which the cutting tool includes a hollow sheath that supports a cutting portion at the cutting tool distal end and the brush is housed within the hollow sheath. Any of the first embodiments may be modified, where possible, to form additional first embodiments in which the cutting portion has cutting edges that are adapted for engaging and cutting tissue upon at least one of rotating and axially translating the cutting tool. Any of the first embodiments may be modified, where possible, to form additional first embodiments in which the outer sheath is configured to convey a vacuum applied at the proximal end to the distal end. Any of the first embodiments may be modified, where possible, to form additional first embodiments in which the outer sheath has at least one opening at its distal end, the cutting tool is retractable toward the outer sheath proximal end and the brush is extendable toward the outer sheath distal end to permit the bristles of the brush to extend through the outer sheath at least one opening. Any of the first embodiments may be modified, where possible, to form additional first embodiments in which the brush can be moved relative to the outer sheath when the brush bristles are extend through the outer sheath at least one opening to permit. Any of the first embodiments may be modified, where possible, to form additional first embodiments in which the outer sheath has at least one port at its distal end, the cutting tool has openings at a cutting portion thereof and is rotatable to align at least one of the openings with the at least one port to permit the bristles of the brush to extend through the outer sheath at least one opening. Any of the first embodiments may be modified, where possible, to form additional first embodiments in which the brush can be moved relative to the outer sheath when the brush bristles are extend through the outer sheath at least one opening to permit. Any of the first embodiments may be modified, where possible, to form additional first embodiments in which the outer sheath has a separate sealed lumen that is isolated from a main lumen containing the cutting tool and brush to permit it to be guided by a wire. Any of the first embodiments may be modified, where possible, to form additional first embodiments in which the outer sheath has a separate sealed lumen that is isolated from a main lumen containing the cutting tool and brush to permit it to be guided by a wire.

According to second embodiments, the disclosed subject matter includes an elongate outer sheath with one or more distal ports at a distal end thereof. An inner sheath has one or more ports alignable with the distal ports. A brush is enclosed within the inner sheath. The inner sheath is movable relative to the outer sheath and brush to permit the bristles thereof to extend through the distal ports.

Any of the second embodiments may be modified, where possible, to form additional second embodiments in which the inner sheath is rotatable within the outer sheath. Any of the second embodiments may be modified, where possible, to form additional second embodiments in which the inner sheath is translatable within the outer sheath. Any of the second embodiments may be modified, where possible, to form additional second embodiments in which the inner or outer sheath has at least one cutting edge to permit tissue projecting into the ports to be sliced.

According to third embodiments, the disclosed subject matter includes a method of using the device of any above claim. The method includes inserting the outer sheath in a tissue and exposing the brush. The method further includes drawing the brush within the inner sheath by moving the inner sheath relative to the outer sheath and withdrawing the outer sheath. The method further includes harvesting cells on the brush.

Any of the third embodiments may be modified, where possible, to form additional third embodiments that include, after the brush is confined within the inner sheath, cutting tissue by moving the inner sheath relative to the outer sheath. Any of the third embodiments may be modified, where possible, to form additional third embodiments that include applying a vacuum to the outer sheath.

According to fourth embodiments, the disclosed subject matter includes a method of performing a biopsy including inserting a catheter in a body lumen and extending brush bristles radially from a distal end of the catheter, scraping the body lumen and withdrawing the bristles radially. The fourth embodiment methods include withdrawing the catheter and retrieving samples from the brush.

Any of the fourth embodiments may be modified, where possible, to form additional fourth embodiments that include applying a vacuum to a proximal end of the catheter and conveying the vacuum to the distal end while performing the scraping. Any of the fourth embodiments may be modified, where possible, to form additional fourth embodiments in which the scraping includes displacing the bristles of the brush and bristles of the brush are supported by the catheter when the catheter is displaced. Any of the fourth embodiments may be modified, where possible, to form additional fourth embodiments that include, the extending includes extending the bristles in opposing directions about an axis of the catheter. Any of the fourth embodiments may be modified, where possible, to form additional fourth embodiments in which the bristles extend through openings in the catheter. Any of the fourth embodiments may be modified, where possible, to form additional fourth embodiments in which the catheter contains a brush and a cutting tool and the method further includes drawing tissue of the lumen into the openings by applying a suction and cutting the tissue with the cutting tool without removing the brush from the catheter. Any of the fourth embodiments may be modified, where possible, to form additional fourth embodiments in which the body lumen is a pancreaticobiliary stricture. Any of the fourth embodiments may be modified, where possible, to form additional fourth embodiments in which a proximal portion of the catheter is supported by an endoscope. Any of the fourth embodiments may be modified, where possible, to form additional fourth embodiments that include inserting a steerable guide wire.

According to fifth embodiments, the disclosed subject matter includes a method of sampling tissue from a body lumen. The method includes inserting an endoscope in a body passage and passing a guide wire into a further body passage to which access is provided by a portion of the endoscope. The method includes guiding a catheter housing a brush to a location in the further body passage along the guide wire. The method includes positioning a distal portion of the catheter at a predefined location of the further body passage. The method includes extending bristles of the brush from the distal portion and disrupting a target surface of the further body passage with the bristles while the bristles are positioned at a longitudinal position of the distal portion and are thereby supported by the catheter without extending distally from it.

Any of the fifth embodiments may be modified, where possible, to form additional fifth embodiments in which the extending includes extending the bristles radially from an axis of the catheter. Any of the fifth embodiments may be modified, where possible, to form additional fifth embodiments in which the distal portion has an opening that faces radially away from an axis of the catheter and the bristles are extended through the opening during the extending. Any of the fifth embodiments may be modified, where possible, to form additional fifth embodiments that include withdrawing the brush while maintaining a position of the distal portion in the further body passage. Any of the fifth embodiments may be modified, where possible, to form additional fifth embodiments that include advancing a cutting tool in the catheter such that a cutting edge traverses the opening and acquiring a slice of tissue from the further body passage. Any of the fifth embodiments may be modified, where possible, to form additional fifth embodiments that include generating a vacuum in the catheter while advancing the cutting tool. Any of the fifth embodiments may be modified, where possible, to form additional fifth embodiments in which the brush is coaxially aligned with the cutting tool. Any of the fifth embodiments may be modified, where possible, to form additional fifth embodiments that include, withdrawing the brush while maintaining a position of the distal portion in the further body passage. Any of the fifth embodiments may be modified, where possible, to form additional fifth embodiments in which the further body passage includes a pancreaticobiliary duct. Any of the fifth embodiments may be modified, where possible, to form additional fifth embodiments in which the positioning includes aligning fiducial markers using fluoroscopy.

According to sixth embodiments, the disclosed subject matter includes a method of sampling tissue from a body lumen including inserting an endoscope in a body passage and passing a guide wire into a further body passage to which access is provided by a portion of the endoscope. The method includes guiding a catheter housing a cutting tool to a location in the further body passage along the guide wire. The method further includes positioning a distal portion of the catheter at a predefined location of the further body passage. The method further includes moving the cutting tool to remove a sample of the further body passage and recovering the sample.

Any of the sixth embodiments may be modified, where possible, to form additional sixth embodiments in which the moving the cutting tool includes displacing it rotationally. Any of the sixth embodiments may be modified, where possible, to form additional sixth embodiments in which the moving the cutting tool includes displacing it axially. Any of the sixth embodiments may be modified, where possible, to form additional sixth embodiments in which the distal portion has an opening that faces radially away from an axis of the catheter and the cutting tool has a cutting edge that can be moved across the opening. Any of the sixth embodiments may be modified, where possible, to form additional sixth embodiments that include withdrawing the cutting tool while maintaining a position of the distal portion in the further body passage. Any of the sixth embodiments may be modified, where possible, to form additional sixth embodiments that include advancing a brush in the catheter and using the brush to disrupt tissue in the further body passage. Any of the sixth embodiments may be modified, where possible, to form additional sixth embodiments that include generating a vacuum in the catheter while advancing the cutting tool. Any of the sixth embodiments may be modified, where possible, to form additional sixth embodiments in which the brush is coaxially aligned with the cutting tool. Any of the sixth embodiments may be modified, where possible, to form additional sixth embodiments in which the further body passage includes a pancreaticobiliary duct.

According to seventh embodiments, the disclosed subject matter includes a catheter that includes a catheter device having an outer sheath with a longitudinal aspect, generally cylindrical in shape, and presenting a smooth surface over an outer radius of the outer sheath. The catheter device is configured such that bristles may be selectively directed from the catheter device at a distal end thereof such that at least some bristle tips extend to a radius greater than the outer sheath outer radius. At least some of the bristles are positioned proximal of the very distal end of the outer sheath such that the bristles receive mechanical support from the catheter device outer sheath. The catheter device is configured such that the bristles may be selectively repositioned such that they are confined within the outer sheath outer radius. The catheter device outer sheath has at least one opening, the catheter device having a cutting tool movable within the outer sheath to move across at least a portion of the at least one opening. The catheter device outer sheath is sized to permit insertion in a human bile duct.

Any of the seventh embodiments may be modified, where possible, to form additional seventh embodiments in which the catheter device outer sheath has an outer diameter of no more than 20 mm. Any of the seventh embodiments may be modified, where possible, to form additional seventh embodiments in which the catheter device outer sheath has an outer diameter of no more than 15 mm. Any of the seventh embodiments may be modified, where possible, to form additional seventh embodiments in which the catheter device outer sheath has an outer diameter of no more than 10 mm. Any of the seventh embodiments may be modified, where possible, to form additional seventh embodiments in which the catheter device outer sheath has an outer diameter of no more than 7 mm. Any of the seventh embodiments may be modified, where possible, to form additional seventh embodiments in which the catheter device outer sheath has an outer diameter of no more than 5 mm. Any of the seventh embodiments may be modified, where possible, to form additional seventh embodiments in which the cutting tool is movable axially within the outer sheath. Any of the seventh embodiments may be modified, where possible, to form additional seventh embodiments in which the bristles are supported on a shaft housed within the outer sheath and are selectively extendable through the at least one opening. Any of the seventh embodiments may be modified, where possible, to form additional seventh embodiments in which the bristles are attached to the cutting tool. Any of the seventh embodiments may be modified, where possible, to form additional seventh embodiments in which the bristles are supported on a shaft housed within the outer sheath and are selectively extendable through the at least one opening. Any of the seventh embodiments may be modified, where possible, to form additional seventh embodiments that include a support instrument that supports the catheter at the proximal end thereof. Any of the seventh embodiments may be modified, where possible, to form additional seventh embodiments that include an endoscope configured to support the catheter at a proximal end thereof and provide actuators for causing the selective repositioning of the bristles.

According to eighth embodiments, the disclosed subject matter includes a biliary sampling catheter with an outer sheath that carries bristles extendable in a radial direction from a distal end of the outer sheath within a longitudinal extent of the outer sheath. The outer sheath has at least one opening for with a cutting tool having a cutting edge that is movable across the at least one opening and adapted for cutting tissue samples of a body lumen. The bristles and the cutting tool may be moved by applying axial forces to a shaft within the outer sheath from a proximal end thereof.

Any of the eighth embodiments may be modified, where possible, to form additional eighth embodiments in which the bristles and the cutting tool may be moved by applying axial forces to a respective shaft or sheath within the outer sheath from a proximal end thereof. Any of the eighth embodiments may be modified, where possible, to form additional eighth embodiments in which the bristles are attached to the cutting tool. Any of the eighth embodiments may be modified, where possible, to form additional eighth embodiments in which the cutting tool is selectively reconfigurable between a cutting configuration and a brushing configuration, in the cutting configuration, the bristles are radially retracted, and in the brushing configuration, the bristles are radially extended such that they can extend through the at least one opening. Any of the eighth embodiments may be modified, where possible, to form additional eighth embodiments in which the at least one opening has a length that permits the bristles to be moved axially in a brushing motion while extended therethrough. Any of the eighth embodiments may be modified, where possible, to form additional eighth embodiments in which bristles are attached to a shaft which extends to a proximal end of the outer sheath and is enclosed within the sheath. Any of the eighth embodiments may be modified, where possible, to form additional eighth embodiments in which the cutting tool is a cylindrical member attached to an inner sheath, within the outer sheath, that can be rotated or moved axially from a proximal end of the outer sheath to move the cutting edge.

According to ninth embodiments, the disclosed subject matter includes a brush catheter that includes a brush on the end of a shaft and an outer sheath encasing the brush and shaft to form a brush catheter assembly. The shaft is movable between a brushing position and an insertion position. The insertion position is such that the brush is entirely encased within the outer sheath such that the outer sheath presents a smooth outer surface for insertion in a body lumen. The brushing position is such that bristles of the brush extend through one or more openings in the outer sheath. In both the brushing and insertion positions, the brush remaining proximal of the very distal end of the outer sheath.

Any of the ninth embodiments may be modified, where possible, to form additional ninth embodiments in which a cutting tool, the cutting tool and brush being movable within the outer sheath such that they can switch places, whereby the cutting tool can be used for cutting tissue extending through the one or more openings and the brush can be used for brushing a body lumen into which the catheter is inserted without fully removing either from the catheter. Any of the ninth embodiments may be modified, where possible, to form additional ninth embodiments in which the brush and the cutting tool may be moved by applying axial forces to a shaft within the outer sheath from a proximal end thereof. Any of the ninth embodiments may be modified, where possible, to form additional ninth embodiments in which the cutting tool is on an inner sheath and the brush is on a shaft, the shaft being within the inner sheath. Any of the ninth embodiments may be modified, where possible, to form additional ninth embodiments in which the brush and the cutting tool may be moved by applying axial forces to a respective shaft or sheath within the outer sheath from a proximal end thereof. Any of the ninth embodiments may be modified, where possible, to form additional ninth embodiments in which the brush is attached to the cutting tool. Any of the ninth embodiments may be modified, where possible, to form additional ninth embodiments in which the cutting tool is selectively reconfigurable between a cutting configuration and a brushing configuration, in the cutting configuration, the bristles are radially retracted, in the brushing configuration, the bristles are radially extended such that they can extend through the at least one opening. Any of the ninth embodiments may be modified, where possible, to form additional ninth embodiments in which the at least one opening has a length that permits bristles of the brush to be moved axially in a brushing motion while extended therethrough. Any of the ninth embodiments may be modified, where possible, to form additional ninth embodiments in which the at least one opening has a length that permits bristles of the brush to be moved axially in a brushing motion while extended therethrough. Any of the ninth embodiments may be modified, where possible, to form additional ninth embodiments in which the bristles are attached to a shaft which extends to a proximal end of the outer sheath and is enclosed within the sheath. Any of the ninth embodiments may be modified, where possible, to form additional ninth embodiments in which the cutting tool is a cylindrical member attached to an inner sheath, within the outer sheath, that can be rotated or moved axially from a proximal end of the outer sheath to move the cutting edge.

According to tenth embodiments, the disclosed subject matter includes a brush catheter that includes an outer sheath having brush and a distal opening through which the brush may be extended and an inner sheath or shaft contained within outer sheath. An expanding member is configured to selectively form a rigid bridge, or to increase a rigidity of a connection between, between the inner sheath or shaft and the brush. Any of the tenth embodiments may be modified, where possible, to form additional tenth embodiments in which the expanding member includes a balloon. Any of the tenth embodiments may be modified, where possible, to form additional tenth embodiments in which the expanding member is within the inner sheath or shaft.

According to eleventh embodiments, the disclosed subject matter includes a method of sampling cells. The method includes inserting a catheter in a body lumen and extending bristles of a brush radially from a distal end of the catheter such that the bristles are within an axial extent of the catheter. The method further includes moving the bristles relative to an outer sheath of the catheter to obtain sample material from the body lumen and moving the bristles into the outer sheath with sample material. The method further includes withdrawing the catheter and recovering the sample material.

Any of the eleventh embodiments may be modified, where possible, to form additional eleventh embodiments in which the catheter of any of the tenth embodiment is used to perform the method. Any of the eleventh embodiments may be modified, where possible, to form additional eleventh embodiments that include, after moving the bristles into the outer sheath, allowing a portion of the body lumen to extend into the outer sheath and slicing it. Any of the eleventh embodiments may be modified, where possible, to form additional eleventh embodiments in which the slicing is performed while the bristles are in the outer sheath. Any of the eleventh embodiments may be modified, where possible, to form additional eleventh embodiments that include passing a brush within a cutting tool to move the cutting tool into position for performing the slicing.

According to twelfth embodiments, the disclosed subject matter includes devices according to any of the above non-method embodiments further including, if not specified, a guide wire, wherein the catheter is configured to follow the guide wire.

According to thirteenth embodiments, the disclosed subject matter includes a brush sampling device that includes an outer sheath having brush carried on an inner sheath, the outer sheath having a distal opening through which the brush may be extended using the inner sheath. A guide wire is inside the inner sheath and a balloon catheter is on the guide wire, the balloon catheter having a shaft with a lumen through which the guide wire passes. The balloon catheter shaft is inserted through the inner sheath to permit the brush to move therealong guided by the balloon catheter. The guide wire, shaft, and inner sheath are extendable through the distal opening.

According to fourteenth embodiments, the disclosed subject matter includes a method of using the thirteenth embodiments, the method including positioning the guide wire in the entrance of a body lumen portion and extending the balloon catheter over the guide wire and positioning it in the body lumen at a point distal of the entrance. The method further includes expanding the balloon to anchor it in the body lumen and extending the brush and brushing the entrance.

Any of the fourteenth embodiments may be modified, where possible, to form additional fourteenth embodiments in which extending includes extending to a point distal of the distal opening. Any of the fourteenth embodiments may be modified, where possible, to form additional fourteenth embodiments that include moving the brush back into the outer sheath, withdrawing the outer sheath with the brush enclosed and protected thereby, and recovering material from the brush. Any of the fourteenth embodiments may be modified, where possible, to form additional fourteenth embodiments that include positioning the catheter using an endoscope. Any of the fourteenth embodiments may be modified, where possible, to form additional fourteenth embodiments that include positioning the catheter near the entrance using an endoscope.

According to fifteenth embodiments, the disclosed subject matter includes a sampling device that includes an elongate outer sheath that simultaneously houses a brush and a cutting tool, the elongate outer sheath being generally adapted for sterilization and insertion in a living person. The elongate outer sheath, the brush, and the cutting tool have respective distal and proximal ends. The brush and cutting tool each has a portion extending over substantially an entire length of the outer sheath. The brush and cutting tool are configured such that each can be manipulated at a respective proximal end thereof to permit the cutting tool to cut tissue samples at the distal outer sheath end and to permit the bristles of the brush selectively to extend outside the outer sheath distal end and retreat back into the outer sheath while the bristles remain within a longitudinal extent of the outer sheath, whereby the brush can be supported by the outer sheath when used for brushing a body lumen into which the outer sheath is inserted. Any of the fifteenth embodiments may be modified, where possible, to form additional fifteenth embodiments in which the outer sheath has radially-facing openings in a distal end thereof and the bristles are extendable in a radial direction through the openings. Any of the fifteenth embodiments may be modified, where possible, to form additional fifteenth embodiments in which the cutting tool and brush are configured such that they can switch positions inside the outer sheath. Any of the fifteenth embodiments may be modified, where possible, to form additional fifteenth embodiments in which the cutting tool and brush are configured such that they can switch positions inside the outer sheath by the brush fitting through the cutting tool. Any of the fifteenth embodiments may be modified, where possible, to form additional fifteenth embodiments in which the cutting tool is generally cylindrical in shape. Any of the fifteenth embodiments may be modified, where possible, to form additional fifteenth embodiments in which the cutting tool and brush are configured such that they can switch positions inside the outer sheath. Any of the fifteenth embodiments may be modified, where possible, to form additional fifteenth embodiments in which the cutting tool and brush are configured such that they can switch positions inside the outer sheath by the brush fitting through the cutting tool. Any of the fifteenth embodiments may be modified, where possible, to form additional fifteenth embodiments in which the cutting tool is generally cylindrical in shape. Any of the fifteenth embodiments may be modified, where possible, to form additional fifteenth embodiments in which the outer sheath is flexible and configured to be guided by a guide wire. Any of the fifteenth embodiments may be modified, where possible, to form additional fifteenth embodiments in which a diameter of the outer sheath is no more than 20 mm. Any of the fifteenth embodiments may be modified, where possible, to form additional fifteenth embodiments in which a diameter of the outer sheath is no more than 15 mm. Any of the fifteenth embodiments may be modified, where possible, to form additional fifteenth embodiments in which a diameter of the outer sheath is no more than 10 mm. Any of the fifteenth embodiments may be modified, where possible, to form additional fifteenth embodiments in which a diameter of the outer sheath is no more than 7 mm. Any of the fifteenth embodiments may be modified, where possible, to form additional fifteenth embodiments in which the cutting tool is attached to an end of an inner sheath and the brush is attached to an end of a shaft, the shaft fitting within the inner sheath.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, sampling catheter devices, systems, and methods. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A sampling device, comprising:
an elongate outer sheath that simultaneously houses a brush and a cutting tool and being generally adapted for sterilization and insertion in a living person;
the elongate outer sheath, the brush, and the cutting tool having distal and proximal ends;
the brush and the cutting tool each having a portion extending over substantially an entire length of the outer sheath;
the brush and the cutting tool being configured such that each can be manipulated at a respective proximal end thereof to permit said cutting tool to cut tissue samples at said distal outer sheath end and to permit said brush selectively to extend outside said outer sheath distal end and retreat back into said outer sheath,
wherein the outer sheath has at least one port at its distal end,
the cutting tool comprises an inner sheath with at least one axially-extending opening at a cutting portion thereof, and
the inner sheath is rotatable relative to the outer sheath so as to align the at least one axially-extending opening with the at least one port so as to permit bristles of the brush to radially extend through said at least one opening of the inner sheath and said at least one port of the outer sheath.

2. The device of claim 1, wherein the inner sheath is hollow and supports the cutting portion at the cutting tool distal end, and the brush is housed within the hollow inner sheath.

3. The device of claim 2, wherein the cutting portion has cutting edges that are adapted for engaging and cutting tissue upon at least one of rotating and axially translating the cutting tool.

4. The device of claim 1, wherein the outer sheath is configured to convey a vacuum applied at the proximal end to the distal end.

5. The device of claim 1, wherein the outer sheath has at least one opening at its distal end, the cutting tool is retractable toward the outer sheath proximal end and the brush is extendable toward the outer sheath distal end to permit bristles of the brush to extend through the outer sheath at least one opening.

6. The device of claim 5, wherein the brush can be moved relative to the outer sheath when the brush bristles extend through the outer sheath at least one opening.

7. The device of claim 1, wherein the brush can be moved relative to the outer sheath when the brush bristles extend through the at least one port of the outer sheath and the at least one opening of the inner sheath.

8. The device of claim 1, wherein the outer sheath has a separate sealed lumen that is isolated from a main lumen containing the cutting tool and brush to permit it to be guided by a wire.

9. The device of claim 1, wherein an edge of the at least one axially extending opening of the inner sheath comprises a cutting edge for said cutting of the tissue samples.

10. A sampling device, comprising:
an elongate outer sheath that simultaneously houses a brush and a cutting tool, the elongate outer sheath being generally adapted for sterilization and insertion in a living person;
the elongate outer sheath, the brush, and the cutting tool having distal and proximal ends;
the brush and the cutting tool each having a portion extending over substantially an entire length of the outer sheath;
the brush and the cutting tool being configured such that each can be manipulated at a respective proximal end thereof to permit said cutting tool to cut tissue samples at said distal outer sheath end and to permit bristles of said brush selectively to extend outside said outer sheath distal end and retreat back into said outer sheath while said bristles remain within a longitudinal extent of said outer sheath, whereby said brush can be supported by said outer sheath when used for brushing a body lumen into which the outer sheath is inserted,
wherein the outer sheath has at least one port at its distal end,
the cutting tool comprises an inner sheath with at least one axially-extending opening at a cutting portion thereof, and
the inner sheath is rotatable relative to the outer sheath such that when the at least one axially-extending opening is aligned with the at least one port, the bristles of the brush can radially extend through said at least one opening of the inner sheath and said at least one port of the outer sheath.

11. The device of claim 10, wherein the outer sheath has radially-facing openings in a distal end thereof and said bristles are extendable in a radial direction through said openings.

12. The device of claim 10, wherein the cutting tool and the brush are configured such that they can switch positions inside said outer sheath.

13. The device of claim 10, wherein the cutting tool and the brush are configured such that they can switch positions inside said outer sheath by said brush fitting through said cutting tool.

14. The device of claim 10, wherein said cutting tool is generally cylindrical in shape.

15. The device of claim 10, wherein said outer sheath is flexible and configured to be guided by a guide wire.

16. The device of claim 10, wherein the brush is attached to an end of a shaft, the shaft fitting within the inner sheath.

* * * * *